United States Patent
He

(10) Patent No.: US 10,329,585 B2
(45) Date of Patent: Jun. 25, 2019

(54) PIV5 AS AN ONCOLYTIC AGENT

(71) Applicant: UNIVERSITY OF GEORGIA RESEARCH FOUNDATION, INC., Athens, GA (US)

(72) Inventor: Biao He, Bogart, GA (US)

(73) Assignee: UNIVERSITY OF GEORGIA RESEARCH FOUNDATION, INC., Athens, GA (US)

(*) Notice: Subject to any disclaimer, the term of this patent is extended or adjusted under 35 U.S.C. 154(b) by 0 days.

(21) Appl. No.: 15/638,946

(22) Filed: Jun. 30, 2017

(65) Prior Publication Data

US 2017/0327845 A1 Nov. 16, 2017

Related U.S. Application Data

(62) Division of application No. 14/374,070, filed as application No. PCT/US2013/022898 on Jan. 24, 2013, now Pat. No. 9,732,358.

(60) Provisional application No. 61/590,070, filed on Jan. 24, 2012, provisional application No. 61/590,056, filed on Jan. 24, 2012, provisional application No. 61/683,810, filed on Aug. 16, 2012.

(51) Int. Cl.
| | |
|---|---|
| C12N 15/86 | (2006.01) |
| A61K 39/155 | (2006.01) |
| C07K 14/115 | (2006.01) |
| C12N 7/00 | (2006.01) |
| C07K 14/005 | (2006.01) |
| A61K 39/12 | (2006.01) |
| A61K 39/04 | (2006.01) |
| A61K 39/145 | (2006.01) |
| A61K 39/205 | (2006.01) |
| A61K 39/00 | (2006.01) |

(52) U.S. Cl.
CPC .............. *C12N 15/86* (2013.01); *A61K 39/04* (2013.01); *A61K 39/12* (2013.01); *A61K 39/145* (2013.01); *A61K 39/155* (2013.01); *A61K 39/205* (2013.01); *C07K 14/005* (2013.01); *C12N 7/00* (2013.01); *A61K 39/00* (2013.01); *A61K 2039/5256* (2013.01); *A61K 2039/53* (2013.01); *A61K 2039/552* (2013.01); *A61K 2039/585* (2013.01); *C12N 2760/16134* (2013.01); *C12N 2760/16171* (2013.01); *C12N 2760/18021* (2013.01); *C12N 2760/18034* (2013.01); *C12N 2760/18721* (2013.01); *C12N 2760/18732* (2013.01); *C12N 2760/18743* (2013.01); *C12N 2760/18771* (2013.01); *C12N 2760/20134* (2013.01); *C12N 2760/20171* (2013.01)

(58) Field of Classification Search
None
See application file for complete search history.

(56) References Cited

U.S. PATENT DOCUMENTS

| | | |
|---|---|---|
| 9,505,807 B2 | 11/2016 | He |
| 2005/0048030 A1 | 3/2005 | Pickels et al. |
| 2006/0275774 A1 | 12/2006 | Olivo et al. |
| 2009/0208495 A1 | 8/2009 | Beier et al. |
| 2010/0119547 A1 | 3/2010 | Haller et al. |
| 2011/0008838 A1 | 1/2011 | Smith et al. |
| 2011/0318355 A1 | 12/2011 | Calatrava et al. |
| 2014/0370050 A1 | 12/2014 | He |
| 2017/0067080 A1 | 3/2017 | He |

FOREIGN PATENT DOCUMENTS

| | | |
|---|---|---|
| WO | WO 1997/041245 A1 | 11/1997 |
| WO | WO 1999/046278 A1 | 9/1999 |
| WO | WO 03/029274 A2 | 4/2003 |
| WO | 2013/112690 A1 | 8/2013 |
| WO | 2013/112720 A1 | 8/2013 |

OTHER PUBLICATIONS

Bissonnette et al., "Analysis of the pH Requirement for Membrane Fusion of Different Isolates of the Paramyxovirus Parainfluenza Virus 5" J Virol, 2006; 80:3071-7.
Gainey et al., "A hyperfusogenic F protein enhances the oncolytic potency of a paramyxovirus simian virus 5 PIV mutant without compromising sensitivity to type I interferon" J Virol, Oct. 2008; 82(19):9369-80. Epub Jul. 30, 2008.
He et al., "Recovery of paramyxovirus simian virus 5 with a V protein lacking the conserved cysteine-rich domain: the multifunctional V protein blocks both interferon-beta induction and interferon signaling" Virology, Nov. 10, 2002; 303(1):15-32.
Parks et al., "Controlled cell killing by a recombinant nonsegmented negative-strand RNA virus" Virology, Feb. 1, 2002; 293(1):192-203.
Suter et al., "In vitro canine distemper virus infection of canine lymphoid cells: a prelude to oncolytic therapy for lymphoma" Clin Cancer Res, Feb. 15, 2005; 11(4): 1579-87.
Tahara et al., "Systemic cancer gene therapy using adeno-associated virus type 1 vector expressing MDA-7/IL24" Mol Ther, Oct. 2007; 15(10):1805-11. Epub Jun. 5, 2007.
Tompkins et al., "Recombinant parainfluenza virus 5 (PIV5) expressing the influenza A virus hemagglutinin provides immunity in mice to influenza A virus challenge" Virology, May 25, 2007; 362(1):139-50. Epub Jan. 23, 2007.

(Continued)

*Primary Examiner* — Nianxiang Zou
(74) *Attorney, Agent, or Firm* — Mueting, Raasch & Gebhardt, P.A.

(57) ABSTRACT

The present invention includes the *Paramyxovirus* Parainfluenza Virus 5 (PIV5) as an oncolytic agent for treating various cancers, including, but not limited to breast cancer, lung cancer and melanoma. PIV5 oncolytic agents include both wild type PIV5 and various recombinant PIV5 constructs. Recombinant PIV5 constructs may include PIV5 lacking the conserved C-terminus of the V protein (PIV5VΔC), PIV5 with mutations in the N-terminus of the V/P protein (PIV5CPI–), and PIV5 expressing MDA-7/IL-24 (rPIV5-MDA7), rPIV5-V/P-CPI–, rPIV5-CPI+, rPIV5-Rev, rPIV5-RL, rPIV5-P-S157A, rPIV5-P-S308A, rPIV5-L-A1981D, rPIV5-F-S443P, rPIV5-MDA7, rPIV5ΔSH-CPI–, or rPIV5ΔSH-Rev. Also included are methods of making and using such oncolytic agents and compositions including such oncolytic agents.

17 Claims, 5 Drawing Sheets

(56) References Cited

OTHER PUBLICATIONS

Wagner et al., "Combined treatment of pediatric high-grade glioma with the oncolytic viral strain MTH-68/H and oral valproic acid." APMIS, Oct. 2006; 114(10):721-43.
Wansley et al., "Naturally occurring substitutions in the PIV gene convert the noncytopathic paramyxovirus simian virus 5 into a virus that induces alpha/beta interferon synthesis and cell death" J Virol, Oct. 2002; 76(20):10109-21.
Young et al., "Simian virus 5 is a poor induced of chemokine secretion from human lung epithelial cells: identification of viral mutants that activate interleukin-8 secretion by distinct mechanisms" J Virol, Jun. 2003; 77(12):7124-30.
International Patent Application No. PCT/US2013/022898, filed Jan. 24, 2013; International Search Report and Written Opinion dated Apr. 10, 2013; 16 pages.
International Patent Application No. PCT/US2013/022898, filed Jan. 24, 2013; International Preliminary Report on Patentability dated Aug. 7, 2014, 8 pages.
ATCC No. VR-399, accessed online on Sep. 14, 2015, at atcc.org/Products/All/VR-399.aspx.
Abraham et al., "Sequential transcription of the genes of vesicular stomatitis virus" Proc Natl Acad Sci USA, 1976; 73:1504-8.
Abrams, "Competition and compensation: coupled to death in development and cancer" Cell, 2002; 110:403-6.
Adusumilli et al., "Real-time diagnostic imaging of tumors and metastases by use of a replication-competent herpes vector to facilitate minimally invasive oncological surgery" The FASEB Journal, 2006; 20(6): 726-8.
Andrejeva et al., "The V proteins of paramyxoviruses bind the IFN-inducible RNA helicase, mda-5, and inhibit its activation of the IFN-{beta} promoter" Proc Natl Acad Sci USA, 2004; 101:17264-9.
Ball et al., "Order of transcription of genes of vesicular stomatitis virus" Proc Natl Acad Sci USA, 1976; 73 :442-6.
Bertram et al., "Establishment of a cloned line of Lewis Lung Carcinoma cells adapted to cell culture" Cancer Lett, 1980; 11(1):63-73.
Bever, "Woman's Cancer Killed by Measles Virus in Unprecedented Trial" The Washington Post, May 15, 2014, Obtained via washingtonpost.com on May 20, 2014.
Bocangel et al., "Combinatorial synergy induced by adenoviral-mediated mda-7 and Herceptin in Her-2+ breast cancer cells" Cancer Gene Ther, 2006; 13:958-68.
Brazil et al., "Ten years of protein kinase B signalling: a hard Akt to follow" Trends Biochem Sci, 2001; 26(11):657-64.
Browning, "Mayo Clinic Trial: Massive blast of measles vaccine wipes out cancer" The Star Tribune, May 14, 2014; Obtained via startribune.com on May 20, 2014.
Chada et al., "MDA-7/IL-24 is a unique cytokine—tumor suppressor in the IL-10 family" Int Immunopharmacol, 2004; 4:649-67.
Chan et al., "AKT/PKB and other D3 phosphoinositide-regulated kinases: kinase activation by phosphoinositide-dependent phosphorylation" Annu Rev Biochem, 1999; 68:965-1014.
Chang et al., "Experimental infection of parainfluenza virus type 5 in mice, hamsters and monkeys" J Immunol, 1965; 95:591-601.
Chatziandreou et al., "Differences in interferon sensitivity and biological properties of two related isolates of simian virus 5: a model for virus persistence" Virology, 2002; 293:234-42.
Chen et al., "Phosphorylated states of vesicular stomatitis virus P protein in vitro and in vivo" Virology, 1997; 228:200-12.
Cohn et al., "T cell responses to the paramyxovirus simian virus 5: studies in multiple sclerosis and normal populations" Pathobiology, 1996; 64:131-5.
Corbett et al., "Response of transplantable tumors of mice to anthracenedione derivatives alone and in combination with clinically useful agents" Cancer Treatment Reports, 1982; 66:1187-200.
Dethlefsen et al., "Analysis of tumor growth curves" J Natl Cancer Inst, 1968; 40:389-405.
Dillon et al., "Exchange of P/V genes between two non-cytopathic simian virus 5 variants results in a recombinant virus that kills cells through death pathways that are sensitive to caspase inhibitors" J Gen Virol, 2006; 87(Pt 12):3643-8.
Du et al. "Regulation of the Akt kinase by interacting proteins" Oncogene, 2005; 24:7401-9.
Duntsch et al., "Recombinant vesicular stomatitis virus vectors as oncolytic agents in the treatment of high-grade gliomas in an organotypic brain tissue slice-glioma coculture model" J Neurosurg, 2004; 100:1049-59.
Ellison et al., "Further evidence to support the melanocytic origin of MDA-MB-435" Mol Pathol, 2002; 55:294-9.
Emerson et al., "Both NS and L proteins are required for in vitro RNA synthesis by vesicular stomatitis virus" J Virol, 1975; 15:1348-56.
Emerson, "Reconstitution studies detect a single polymerase entry site on the vesicular stomatitis virus genome" Cell, 1982; 31:635-42.
Fielding, "Measles as a potential oncolytic virus" Rev Med Virol, 2005; 15(2):135-42.
Fisher, "Apoptosis in cancer therapy: crossing the threshold" Cell, 1994; 78:539-42.
Fuentes et al., "Function of the respiratory syncytial virus small hydrophobic protein" J Virol, 2007; 81:8361-6.
Gopalkrishnan et al., "Cytokine and tumor cell apoptosis inducing activity of mda-7/IL-24" Int Immunopharmacol, 2004; 4(5):635-47.
Hanahan et al., "The hallmarks of cancer" Cell, 2000; 100(1):57-70.
Harms et al., "A small molecule antagonist of the alpha(v)beta3 integrin suppresses MDA-MB-435 skeletal metastasis" Clin Exp Metastasis, 2004; 21(2):119-28.
He et al., "Rapid mutagenesis and purification of phage RNA polymerases" Protein Expr Purif, 1997; 9(1):142-51.
Heise et al., "Intravenous administration of ONYX-015, a selectively replicating adenovirus, induces antitumoral efficacy" Cancer Res, 1999; 59: 2623-8.
Hotte et al., "An Optimized Clinical Regimen for the Oncolytic Virus PV701" Clin Cancer Res, 2007; 13(3):977-85.
Hu et al., "Oncolytic Adenovirus Expressing Soluble TGFbeta Receptor Ii-Femediated Inhibition of Established Bone Metastases: A Safe and Effective Systemic Therapeutic Approach for Breast Cancer" Mol Ther, 2011; 19(9):1609-18.
Huang et al., "High-level expression of a foreign gene from the most 3'-proximallocus of a recombinant Newcastle disease virus" J Gen Virol, 2001; 82:1729-36.
Ishikawa et al., "Expression of MDA-7/IL-24 and Its Clinical Significant in Resected Non-Small Cell Lung Cancer" Clin Cancer Res, 2005; 11:1198-1202.
Iverson et al., "Sequential synthesis of 5'-proximal vesicular stomatitis virus mRNA sequences" J Virol, 1982; 44: 356-5.
Jack et al., "The complete genome sequence of J virus reveals a unique genome structure in the family Paramyxoviridae" J Virol, 2005; 79:10690-700.
Jacques et al., "Pseudo-templated transcription in prokaryotic and eukaryotic organisms" Genes Dev, 1991; 5:707-13.
Johnstone et al., "Apoptosis: a link between cancer genetics and chemotherapy" Cell, 2002; 108:153-64.
Ju et al., "Akt1 governs breast cancer progression in vivo" Proc Natl Acad Sci USA, 2007; 104:7438-43.
Kau et al., "A chemical genetic screen identifies inhibitors of regulated nuclear export of a Forkhead transcription factor in PTEN-deficient tumor cells" Cancer Cell, 2003; 4:463-76.
Kim et al., "Studies on the antiviral mechanisms of protein kinase inhibitors K-252a and KT5926 against the replication of vesicular stomatitis virus" Biol Pharm Bull, 1998; 21(5):498-505.
Kirn et al., "ONYX-015: clinical data are encouraging" Nat Med, 1998; 4(12):1341-1342.
Krishnamurthy et al., "Differentially regulated interferon response determines the outcome of Newcastle disease virus infection in normal and tumor cell lines" J Virol, 2006; 80:5145-55.
Lamb et al., "The synthesis of Sendai virus polypeptides in infected cells. III. Phosphorylation of polypeptides" Virology, 1977; 81(2):382-97.
Lenard, "Host cell protein kinases in nonsegmented negative-strand virus (mononegavirales) infection" Pharmacal Ther, 1999; 83:39-48.

(56) References Cited

OTHER PUBLICATIONS

Li et al., "Beilong virus, a novel paramyxovirus with the largest genome of non-segmented negative-stranded RNA viruses" *Virology*, 2006; 346(1):219-28.
Lin et al., "The RNA binding region of the paramyxovirus SV5 V and P proteins" *Virology*, 1997; 238:460-9.
Lin et al., "The paramyxovirus simian virus 5 V protein slows progression of the cell cycle" *J Virol*, 2000; 74:9152-66.
Lin et al. "Inhibition of interleukin-6 expression by the V protein of parainfluenza virus 5" *Virology*, 2007; 368:262-72.
Liston et al., "Measles virus V protein binds zinc" *Virology*, 1994; 198:399-404.
Lorence et al., "Newcastle disease virus as an antineoplastic agent: induction of tumor necrosis factor-alpha and augmentation of its cytotoxicity" *J Natl Cancer Inst*, 1988; 80(16):1305-12.
Lorence et al., "Overview of phase I studies of intravenous administration of PV701, an oncolytic virus" *Curr Opin Mol Ther*, 2003; 5(6):618-24.
Lu et al., "The Major Phosphorylation Sites of the Respiratory Syncytial Virus Phosphoprotein Are Dispensable for Virus Replication In Vitro" *J Virol*, 2002; 76:10776-84.
Mastro et al., "The skeleton as a unique environment for breast cancer cells" *Clin Exp Metastasis*, 2003; 20(3):275-84.
Mastro et al., "Breast cancer cells induce osteoblast apoptosis: a possible contributor to bone degradation" *J Cell Biochem*, 2004; 91(2):265-76.
Mayo, "Names of viruses and virus species- an editorial note" *Arch Virol*, 2002; 147(7):1463-4.
Morales et al., "Absence of cancer-associated changes in human fibroblasts immortalized with telomerase" *Nat Genet*, 1999; 21(1):115-8.
Myers et al., "Oncolytic activities of approved mumps and measles vaccines for therapy of ovarian cancer" *Cancer Gene Ther*, 2005; 12(7):593-9.
Nishikawa et al., "Adenoviral-mediated mda-7 expression suppresses DNA repair capacity and radiosensitizes non-small-cell lung cancer cells" *Oncogene*, 2004; 23(42):7125-31.
Nishikawa et al., "Adenovirus-mediated mda-7 (IL24) gene therapy suppresses angiogenesis and sensitizes NSCLC xenograft tumors to radiation" *Mol Ther*, 2004; 9:818-28.
Obuchi et al., "Development of recombinant vesicular stomatitis viruses that exploit defects in host defense to augment specific oncolytic activity " *J Virol*, 2003; 77:8843-56.
Parisien et al., "Selective STAT protein degradation induced by paramyxoviruses requires both STAT1 and STAT2 but is independent of alpha/beta interferon signal transduction" *J Virol*, 2002; 76:4190-8.
Parks et al., "Controlled cell killing by a recombinant nonsegmented negative-strand RNA virus" *Virology*, 2002; 293(1):192-203.
Paterson et al., "The paramyxovirus SV5 V protein binds two atoms of zinc and is a structural component of virions" *Virology*, 1995; 208:121-31.
Pecora et al., "Phase I trial of intravenous administration of PV701, an oncolytic virus, in patients with advanced solid cancers" *J Clin Oncol*, 2002; 20(9):2251-66.
Phadke et al., "Kinetics of metastatic breast cancer cell trafficking in bone" *Clin Cancer Res*, 2006; 12:1431-40.
Precious et al., "Inducible expression of the P, V, and NP genes of the paramyxovirus simian virus 5 in cell lines and an examination of NP-P and NP-V interactions" *J Virol*, 1995; 69:8001-10.
Precious et al., "Simian virus 5 V protein acts as an adaptor, linking DDB1 to STAT2, to facilitate the ubiquitination of STAT1" *J Virol*, 2005; 79:13434-441.
Ramesh et al., "Ectopic production of MDA-7/IL-24 inhibits invasion and migration of human lung cancer cells" *Mol Ther*, 2004; 9:510-18.
Randall et al., "NP:P and NP:V interactions of the paramyxovirus simian virus 5 examined using a novel protein:protein capture assay" *Virology*, 1996; 224:121-9.
Redaelli et al. "Synthesis and biological activity of Akt/PI3K inhibitors" *Mini Rev Med Chem*, 2006; 6(10):1127-36.
Ross et al., "Systematic variation in gene expression patterns in human cancer cell lines" *Nat Genet*, 2000; 24(3):227-35.
Rubin et al., "Changes in mumps virus gene sequence associated with variability in neurovirulent phenotype" *J Virol*, 2003; 77:11616-24.
Sarbassov et al., "Phosphorylation and regulation of Akt/PKB by the rictor-mTOR complex" *Science*, 2005; 307(5712):1098-101.
Sauane et al., "Melanoma differentiation associated gene-7/interleukin-24 promotes tumor cell-specific apoptosis through both secretory and nonsecretory pathways" *Cancer Res*; 64:2988-93.
Sellappan et al., "Lineage infidelity of MDA-MB-435 cells: expression of melanocyte proteins in a breast cancer cell line" *Cancer Res*, 2004; 64:3479-85.
Sharma et al., "T cell-derived IL-10 promotes lung cancer growth by suppressing both T cell and APC function" *J Immunol*, 1999; 163:5020-8.
Sharma et al., "Targeting mitogen-activated protein kinase/extracellular signal-regulated kinase kinase in the mutant (V600E) B-Raf signaling cascade effectively inhibits melanoma lung metastases" *Cancer Res*, 2006; 66:8200-09.
Sinkovics et al., "Newcastle disease virus (NDV): brief history of its oncolytic strains" *J Clin Virol*, 2000; 16(1):1-15.
Spadafora et al., "Constitutive phosphorylation of the vesicular stomatitis virus P protein modulates polymerase complex formation but is not essential for transcription or replication" *J Virol*, 1996; 70:4538-48.
Stambolic et al., "Functional distinctions of protein kinase B/Akt isoforms defined by their influence on cell migration" *Trends Cell Biol*, 2006; 16(9):461-6.
Stanziale et al. "Oncolytic herpes simplex virus-1 mutant expressing green fluorescent protein can detect and treat peritoneal cancer" *Hum Gene Ther*, 2004; 15(6): 609-18.
Steward et al., "The Newcastle disease virus V protein binds zinc" *Arch Virol*, 1995; 140(7):1321-8.
Stojdl et al., "Exploiting tumor-specific defects in the interferon pathway with a previously unknown oncolytic virus" *Nat Med*, 2000; 6(7):821-5.
Sun et al., "AKT1/PKBalpha kinase is frequently elevated in human cancers and its constitutive activation is required for oncogenic transformation in NIH3T3 cells" *Am J Pathol*, 2001; 159: 431-7.
Sun et al., "Akt Plays a Critical Role in Replication of Nonsegmented Negative-Stranded RNA Viruses" *J Virol*, 2008; 82:105-114.
Teshigahara et al., "Oncolytic viral therapy for breast cancer with herpes simplex virus type 1 mutant HF 10" *J Surg Oncol*, 2004; 85:42-7.
Thomas et al., "Two mRNAs that differ by two nontemplated nucleotides encode the amino coterminal proteins P and V of the paramyxovirus SV5" *Cell*, 1988; 54(6):891-902.
Thorne et al., "Future directions for the field of oncolytic virotherapy: a perspective on the use of vaccinia virus" *Expert Opin Biol Ther*, 2004; 4(8):1307-21.
Tompkins et al., "Recombinant parainfluenza virus 5 (PIV5) expressing the influenza A virus hemagglutinin provides immunity in mice to influenza A virus challenge" *Virology*, 2007; 362(1):139-50.
Trent et al., "Tumorigenicity in human melanoma cell lines controlled by introduction of human chromosome 6" *Science*, 1990; 247(4942):568-71.
van Weeren et al., "Essential role for protein kinase B (PKB) in insulin-induced glycogen synthase kinase 3 inactivation. Characterization of dominant-negative mutant of PKB" *J Biol Chem*, 1998; 273:13150-6.
Wang et al., "Interleukin 24 (MDA-7/MOB-5) signals through two heterodimeric receptors, IL-22R1/IL-20R2 and IL-20R1/IL-20R2" *J Biol Chem*, 2002; 277:7341-7.
Wansley et al., "Apoptosis induction and interferon signaling but not IFN-beta promoter induction by an SV5 P/V mutant are rescued by coinfection with wild-type SV5" *Virology*, 2003; 316:41-54.
Wansley et al., "Growth sensitivity of a recombinant simian virus 5 P/V mutant to type I interferon differs between tumor cell lines and normal primary cells" *Virology*, 2005; 335:131-44.

(56) References Cited

OTHER PUBLICATIONS

Welch, "Technical considerations for studying cancer metastasis in vivo" *Clin Exp Metastasis*, 1997; 15(3):272-306.
Welch et al., "Molecular biology of breast cancer metastasis. Genetic regulation of human breast carcinoma metastasis" *Breast Cancer Res*, 2000; 2:408-16.
Wildner, "Comparison of replication-selective, oncolytic viruses for the treatment of human cancers" *Curr Opin Mol Ther*, 2003; 5(4):351-61.
Wollmann et al. "Variable deficiencies in the interferon response enhance susceptibility to vesicular stomatitis virus oncolytic actions in glioblastoma cells but not in normal human glial cells" *J Virol*, 2007; 81:1479-91.
Yacoub et al., "MDA-7 regulates cell growth and radiosensitivity in vitro of primary (non-established) human glioma cells" *Cancer Biol Ther*, 2004; 3(8):739-51.
Yang et al., "Human endothelial cell life extension by telomerase expression" *J Biol Chem*, 1999; 274(37):26141-8.
Yin et al., "Structure of the parainfluenza virus 5 F protein in its metastable, prefusion conformation" *Nature*, 2006; 439(7072):38-44.
Yoeli-Lerner et al., "Akt/PKB signaling in cancer: a function in cell motility and invasion" *Cell Cycle*, 2006; 5(6):603-5.
Young et al., "Variants of the paramyxovirus Simian virus 5 with accelerated or delayed viral gene expression activate proinflammatory cytokine synthesis" *Virology*, 2006; 350: 90-102.
Zorn et al., "Induction of cytokines and cytotoxicity against tumor cells by Newcastle disease virus" *Cancer Biother*, 1994; 9(3):225-35.
Zwiebel, "Cancer gene and oncolytic virus therapy" *Semin Oncol*, 2001; 28:336-43.
ATCC No. VR-288, accessed online on Sep. 11, 2015, at atcc.org/Products/All/VR-288.aspx#generalinformation.
ATCC No. VR-1573, accessed online on Sep. 11, 2015, at atcc.org/Products/All/VR-1573.aspx.
International Patent Application No. PCT/US2013/022962, filed Jan. 24, 2013; International Search Report and Written Opinion dated Apr. 10, 2013; 16 pages.
International Patent Application No. PCT/US2013/022962, filed Jan. 24, 2013; International Preliminary Report on Patentability dated Aug. 7, 2014, 12 pages.
European Patent Application No. 13 74 1216.9, filed Aug. 22, 2014; Supplementary European Search Report dated Jul. 20, 2015; 4 pages.
"Influenza fact sheet" *Wkly Epidemiol Rec.*, Mar. 14, 2003; 78(11):77-80.
Adams et al., "The Bcl-2 protein family: arbiters of cell survival" *Science*, 1998; 281(5381):1322-6.
Andrejeva et al., "Degradation of STAT1 and STAT2 by the V proteins of simian virus 5 and human parainfluenza virus type 2, respectively: consequences for virus replication in the presence of alpha/beta and gamma interferons" *J Virol*. 2002; 76:2159-67.
Arimilli et al., "A simian virus 5 (SV5) P/V mutant is less cytopathic than wild-type SV5 in human dendritic cells and is a more effective activator of dendritic cell maturation and function" *J Virol*. 2006; 80:3416-27.
Ashkenazi et al., "Death receptors: signaling and modulation" *Science*, 1998; 281(5381):1305-8.
Atoynatan et al., "Epidemiologic studies of latent virus infections in captive monkeys and baboons. II. Serologic evidence of myxovirus infections with special reference to SV5" *Am J Epidemiol*, 1969; 89(4):472-9.
Azetaka et al., "Kennel cough complex: confirmation and analysis of the outbreak in Japan" *Nippon Juigaku Zasshi*, 1988; 50(4):851-8.
Baez et al., "Gene composition of high-yielding influenza vaccine strains obtained by recombination" *J Infect Dis*, 1980; 141(3):362-5.

Baumgertner et al., "Persistent infection of Vero cells by paramyxoviruses. A morphological and immunoelectron microscopic investigation" *Intervirology*, 1987; 27(4):218-23.
Bernstein et al., "Clinical reactions and serologic responses after vaccination with whole-virus or split-virus influenza vaccines in children aged 6 to 36 months" *Pediatrics*, 1982; 69(4):404-8.
Binn et al., "Viruses recovered from laboratory dogs with respiratory disease" *Proc Soc Exp Bioi Med*, 1967; 126(1):140-5.
Braciale et al., "On the role of the transmembrane anchor sequence of influenza hemagglutinin in target cell recognition by class I MHC-restricted, hemagglutinin-specific cytolytic T lymphocytes" *J Exp Med*, 1987; 166:678-92.
Capraro et al., "Virus growth and antibody responses following respiratory tract infection of ferrets and mice with WT and P/V mutants of the paramyxovirus Simian Virus 5" *Virology*, Jul. 5, 2008; 376(2):416-28.
Centers for Disease Control and Prevention (CDC), "Possible congenital infection with La Crosse encephalitis virus—West Virginia, 2006-2007" *MMWR Morb Mortal Wkly Rep*, 2009; 58(1):4-7.
Chatziandreou et al., "Relationships and host range of human, canine, simian and porcine isolates of simian virus 5 (parainfluenza virus 5)" *J Gen Virol*, 2004; 85(Pt 10):3007-16.
Chen et al., "Protection and antibody responses in different strains of mouse immunized with plasmid DNAs encoding influenza virus haemagglutinin, neuraminidase and nucleoprotein" *J Gen Virol*, 1999; 80(Pt 10):2559-64.
Chen et al., "Identification of two auto-cleavage products of nonstructural protein 1 (nsp1) in porcine reproductive and respiratory syndrome virus infected cells: nsp1 function as interferon antagonist" *Virology*, 2010; 398(1):87-97.
Chen et al., "Evaluating a Parainfluenza Virus 5-Based Vaccine in a Host with Pre-Existing Immunity against Parainfluenza Virus 5" *PLoS One*, 2012; 7(11):e50144, doi: 10.1371/journal.pone.0050144, Epub Nov. 20, 2012.
Chen et al., "A novel rabies vaccine based on a recombinant parainfluenza virus 5 expressing rabies virus glycoprotein," *J Virol*; Dec. 26, 2012; [Epub ahead of print], doi:10.1128/JVI.02886-12.
Chladek et al., "Canine parainfluenza-Bordetella bronchiseptica vaccine Immunogenicity" *Am J Vet Res*, 1981; 42(2):266-70.
Choppin, "Multiplication of a myxovirus (SV5) with minimal cytopathic effects and without interference" *Virology*, 1964; 23:224-33.
Clark et al., "Parainfluenza virus 5-based vaccine vectors expressing vaccinia virus (VACV) antigens provide long-term protection in mice from lethal intranasal VACV challenge" *Virology*, 2011; 419(2):97-106.
Cornwell et al., "Isolation of parainfluenza virus SV5 from dogs with respiratory disease" *Vet Rec*, 1976; 98(15):301-2.
Cory et al., "The Bcl2 family: regulators of the cellular life-or-death switch" *Nat Rev Cancer*, 2002; 2(9):647-56.
Cox et al., "Rabies virus glycoprotein: II. Biological and serological characterization" *Infect Immun*, 1977; 16:754-9.
Crawford et al., "Baculovirus-derived hemagglutinin vaccines protect against lethal influenza infections byavianH5 andH7 subtypes" *Vaccine*, 1999; 17(18):2265-74.
Crawford et al., "Transmission of equine influenza virus to dogs" *Science*, 2005; 310(5747):482-5.
Daly et al., "Transmission of equine influenza virus to English foxhounds" *Emerg Infect Dis*, 2008; 14:461-4.
Didcock et al., "The V protein of simian virus 5 inhibits interferon signalling by targeting STAT1 for proteasome-mediated degradation" *J Virol*, 1999; 73:9928-33.
Driskell et al., "One-step assay for detecting influenza virus using dynamic light scattering and gold nanoparticles" *Analyst*, 2011; 136(15):3083-90.
Emery et al., "A canine parainfluenza viral vaccine: immunogenicity and safety" *Am J Vet Res*, 1976; 37(11):1323-7.
Enserink, "Avian influenza. 'Pandemic vaccine' appears to protect only at high doses" *Science*, 2005; 309(5737):996.
Epstein, et al. "Mechanisms of heterosubtypic immunity to lethal influenza A virus infection in fully immunocompetent, T cell-depleted, beta2-microglobulin-deficient, and J chain-deficient mice" *J Immunol*, 1997; 158(3):1222-30.

(56) References Cited

OTHER PUBLICATIONS

Epstein et al., "DNA vaccine expressing conserved influenza virus proteins protective against H5N1 challenge infection in mice" *Emerg Infect Dis*, 2002; 8:796-801.
Epstein, "Control of influenza virus infection by immunity to conserved viral features" *Expert Rev Anti Infect Ther*, 2003; 1(4):627-38.
Epstein et al., "Protection against multiple influenza A subtypes by vaccination with highly conserved nucleoprotein" *Vaccine*, 2005; 23(46-47):5404-10.
Evan et al., "A matter of life and cell death" *Science*, 1998; 281(5381):1317-22.
Evermann et al., "Isolation of a paramyxovirus from the cerebrospinal fluid of a dog with posterior paresis" *J Am Vet Med Assoc*, 1980; 177(11):1132-4.
Evermann et al., "Properties of an encephalitogenic canine parainfluenza virus" *Arch Virol*, 1981; 68:165-72.
Faber et al., "Immunogenicity and safety of recombinant rabies viruses used for oral vaccination of stray dogs and wildlife" *Zoonoses Public Health*, 2009; 56(6-7):262-9.
Flynn et al., "Virus-specific CD8+ T cells in primary and secondary influenza pneumonia" *Immunity*, 1998; 8(6):683-91.
Fouchier et al., "Characterization of a novel influenza A virus hemagglutinin subtype (H16) obtained from black-headed gulls" *J Virol*, 2005; 79:2814-22.
Gabbard et al., "A humanized anti-M2 scFv shows protective in vitro activity against influenza" *Prot Eng Des Sel*, 2009; 22:189-98.
Gainey et al., "A Hyperfusogenic F Protein Enhances the Oncolytic Potency of a Paramyxovirus Simian Virus 5 P/V Mutant without Compromising Sensitivity to Type I Interferon" *J Virol*, 2008; 82(19):9369-80.
Ge et al., "Newcastle disease virus-vectored rabies vaccine is safe, highly immunogenic, and provides long-lasting protection in dogs and cats" *J Virol*, 2011; 85:8241-52.
Gerhard et al., "Identification of eight determinants in the hemagglutinin molecule of influenza virus A/PR/8/34 (H1N1) which are recognized by class II-restricted T cells from BALB/c mice" *J Virol*, 1991; 65:364-72.
Goff et al., "Construction of hybrid viruses containing SV40 and lambda phage DNA segments and their propagation in cultured monkey cells" *Cell*, 1976; 9(4 Pt 2):695-705.
Goswami et al., "Does simian virus 5 infect humans?" *J Gen Virol*, 1984; 65(Pt 8):1295-303.
Goswami et al., "Antibodies against the paramyxovirus SV5 in the cerebrospinal fluids of some multiple sclerosis patients" *Nature*, 1987; 327(6119): 244-7.
Govorkova et al., "Lethality to ferrets of H5N1 influenza viruses isolated from humans and poultry in 2004" *J Virol*, 2005; 79(4):2191-8.
Graham et al. "Resistance to and recovery from lethal influenza virus infection in B lymphocyte-deficient mice" *J Exp Med*, 1997; 186(12):2063-8.
Gross et al., "BCL-2 family members and the mitochondria in apoptosis" *Genes Dev*, 1999; 13:1899-911.
Hallak et al., "Iduronic acid-containing glycosaminoglycans on target cells are required for efficient respiratory syncytial virus infection" *Virology*, 2000; 271(2):264-75.
Harper et al., "Prevention and control of influenza. Recommendations of the Advisory Committee on Immunization Practices (ACIP)" *MMWR Recomm Rep*, 2005; 54(RR-8):1-40.
He et al., "Phage RNA polymerase vectors that allow efficient gene expression in both prokaryotic and eukaryotic cells" *Gene*, 1995; 164:75-9.
He et al., "Recovery of infectious SV5 from cloned DNA and expression of a foreign gene" *Virology*, 1997; 237:249-60.
He et al., "The paramyxovirus SV5 small hydrophobic (SH) protein is not essential for virus growth in tissue culture cells" *Virology*, 1998; 250:30-40.
He et al., "Effect of inserting paramyxovirus simian virus 5 gene junctions at the HN/L gene junction: analysis of accumulation of mRNAs transcribed from rescued viable viruses" *J Virol*, 1999; 73:6228-34.
He et al., "The SH integral membrane protein of the paramyxovirus simian virus 5 is required to block apoptosis in mdbk cells" *J Virol*, 2001; 75:4068-79.
He et al., "Recovery of paramyxovirus simian virus 5 with a V protein lacking the conserved cysteine-rich domain: the multifunctional V protein blocks both interferon-beta induction and interferon signaling" *Virology*, 2002; 303:15-32.
Hiebert et al., "Cell surface expression and orientation in membranes of the 44 amino acid SH protein of simian virus 5" *J Virol*, 1988; 62:2347-57.
Hoffmann et al., "Role of specific hemagglutinin amino acids in the immunogenicity and protection of H5N1 influenza virus vaccines" *Proc Natl Acad Sci USA*, 2005; 102:12915-20.
Horimoto et al., "Reverse genetics provides direct evidence for a correlation of hemagglutinin cleavability and virulence of an avian influenza A virus" *J Virol*, 1994; 68(5):3120-8.
Hsiung et al., "Studies of Parainfluenza Viruses. 3. Antibody Responses of Different Animal Species After Immunization" *J Immunol*, 1965; 94:67-73.
Hsiung "Parainfluenza-5 virus. Infection of man and animal" *Prog Med Virol*, 1972; 14:241-74.
Huang et al., "Parainfluenza virus 5 expressing the G protein of rabies virus protect mice after rabies virus infection" *J Virol*, 2015; 89(6):3427-9.
Hull et al., "New viral agents recovered from tissue cultures of monkey kidney cells. 1. Origin and properties of cytopathic agents $S.V._1$, $S.V._2$, $S.V._4$, $S.V._5$, $S.V._6$, $S.V._{11}$, $S.V._{12}$, and $S.V._{15}$" *Am J Hyg*, 1956; 63(2):204-15.
Jin et al, "Palmitylation of the influenza virus hemagglutinin (H3) is not essential for virus assembly or infectivity" *J Virol*, 1996; 70:1406-14.
Katz et al., "Molecular correlates of influenza a H5N1 virus pathogenesis in mice" *J Virol*, 2000; 74:10807-10.
Kieny et al., "Expression of rabies virus glycoprotein from a recombinant vaccinia virus" *Nature*, 1984; 312(5990):163-6.
Knobel et al., "Re-evaluating the burden of rabies in Africa and Asia" *Bull World Health Organ*, 2005; 83:360-8.
Komada et al., "Immunological relationships between parainfluenza virus type 4 and other paramyxoviruses studied by use of monoclonal antibodies" *Arch Virol*, 1991; 116(1-4):277-83.
Kong et al., "Protective immunity to lethal challenge of the 1918 pandemic influenza virus by vaccination" *Proc Natl Acad Sci USA*, 2006; 103(43)15987-91.
Kontor et al., "Canine infectious tracheobronchitis: effects of an intranasal live canine parainfluenza-Bordetella bronchiseptica vaccine on viral shedding and clinical tracheobronchitis (kennel cough)" *Am J Vet Res*, 1981; 42(10):1694-8.
Kretzschmar et al., "High-Efficiency Incorporation of Functional Influenza Virus Glycoproteins into Recombinant Vesicular Stomatitis Viruses" *J Virol*, 1997; 71(8):5982-9.
Krunkosky et al., "Effects of TNF-alpha on expression of ICAM-1 in human airway epithelial cells in vitro. Signaling pathways controlling surface and gene expression" *Am J Respir Cell Mol Biol*, 2000; 22(6):685-92.
Lawson et al., "Primary pulmonary cytotoxic T lymphocytes induced by immunization with a vaccinia virus recombinant expressing influenza A virus nucleoprotein peptide do not protect mice against challenge" *J Virol*, 1994; 68(6):3505-11.
Li et al., "Recombinant influenza A virus vaccines for the pathogenic human A/Hong Kong/97 (H5N1) viruses" *J Infect Dis*, 1999; 179:1132-8.
Li et al., "A single immunization with a recombinant canine adenovirus expressing the rabies virus G protein confers protective immunity against rabies in mice" *Virology*, 2006; 356:147-54.
Li et al., "Avian-origin H3N2 canine influenza A viruses in Southern China" *Infect Genet Evol*, 2010; 10:1286-8.
Li et al., "Recombinant Parainfluenza Virus 5 Expressing Hemagglutinin of Influenza A Virus H5N1 Protected Mice against Lethal

(56) References Cited

OTHER PUBLICATIONS

Highly Pathogenic Avian Influenza Virus H5N1 Challenge," *J Virol*, Jan. 2013; 87(1):354-62. doi: 10.1128/JVI.02321-12. Epub Oct. 17, 2012.
Li et al., "Single-Dose Vaccination of a Recombinant Parainfluenza Virus 5 Expressing NP from H5N1 Virus Provides Broad Immunity against Influenza A Viruses" *J Virol*, May 2013, 87(10):5985-93.
Lin et al., "The V protein of the paramyxovirus SV5 interacts with damage-specific DNA binding protein" *Virology*, 1998; 249:189-200.
Lin et al., "Induction of apoptosis by paramyxovirus simian virus 5 lacking a small hydrophobic gene" *J Virol*, 2003; 77:3371-83.
Lin et al., "The role of simian virus 5 V protein on viral RNA synthesis" *Virology*, 2005; 338:270-80.
Lipatov et al., "Influenza: emergence and control" *J Virol*, 2004; 78:8951-9.
Lipatov et al., "Efficacy of H5 influenza vaccines produced by reverse genetics in a lethal mouse model" *J Infect Dis*, 2005; 191:1216-20.
Lipatov et al., "Cross-protectiveness and immunogenicity of influenza A/Duck/Singapore/3/97(H5) vaccines against infection with A/Vietnam/1203/04(H5N1) virus in ferrets" *J Infect Dis*, 2006; 194:1040-3.
Liu et al., "Preparation of a standardized, efficacious agricultural H5N3 vaccine by reverse genetics" *Virology*, 2003; 314:580-90.
Lu et al., "A mouse model for the evaluation of pathogenesis and immunity to influenza A (H5N1) viruses isolated from humans" *J Virol*, 1999; 73:5903-11.
Maeda et al., "Live Bivalent Vaccine for Parainfluenza and Influenza Virus Infections" *J Virol*, 2005; 79(11):6674-9.
Martinez, "Global infectious disease surveillance" *Int J Infect Dis*, 2000; 4(4):222-8.
McCandlish et al., "A study of dogs with kennel cough" *Vet Rec*, 1978; 102(14):293-301.
Meslin et al., "Rationale and prospects for rabies elimination in developing countries" *Curr Top Microbiol Immunol*, 1994; 187:1-26.
Mooney, "PIV5 as a Novel Vaccine Vector for Pandemic Influenza" PhD Thesis, 2012; Retrieved online Oct. 1, 2015 from getd.libs.ega.edu/pdfs/mooney_alaina_j_201205_phd. pdf.
Mooney et al., "Recombinant Parainfluenza Virus 5 Vaccine Encoding the Influenza Virus Hemagglutinin Protects against H5N1 Highly Pathogenic Avian Influenza Virus Infection following Intranasal or Intramuscular Vaccination of BALB/c Mice" *J Virol*, 2013; 87(1):363-71.
Murphy et al., "Genome nucleotide lengths that are divisible by six are not essential but enhance replication of defective interfering RNAs of the paramyxovirus simian virus 5" *Virology*, 1997; 232:145-57.
Murray et al., "Rabies in vaccinated dogs and cats in the United States, 1997-2001" *J Am Vet Med Assoc*, 2009; 235(6):691-5.
Nakaya et al., "Recombinant Newcastle disease virus as a vaccine vector" *J Virol*, 2001; 75:11868-73.
Nayak et al., "Contributions of the avian influenza virus HA, NA, and M2 surface proteins to the induction of neutralizing antibodies and protective immunity" *J Virol*, 2010; 84(5):2408-20.
Neirynck et al., "A universal influenza A vaccine based on the extracellular domain of the M2 protein" *Nat Med*, 1999; 5(10):1157-63.
Okuda et al., "Protective immunity against influenza A virus induced by immunization with DNA plasmid containing influenza M gene" *Vaccine*, 2001; 19(27):3681-91.
Palese, "Genetic engineering of infectious negative-strand RNA viruses" *Trends Microbiol*, 1995; 3(4):123-5.
Parks et al., "Increased readthrough transcription across the simian virus 5 M-F gene junction leads to growth defects and a global inhibition of viral mRNA synthesis" *J Virol*, 2001; 75:2213-23.
Parks et al., "High avidity cytotoxic T lymphocytes to a foreign antigen are efficiently activated following immunization with a recombinant paramyxovirus, simian virus 5" *J Gen Virol*, 2002; 83(Pt 5):1167-72.
Paterson et al., "Fusion protein of the paramyxovirus SV5: destabilizing and stabilizing mutants of fusion activation" *Virology*, 2000; 270:17-30.
Pekosz et al., "Reverse genetics of negative-strand RNA viruses: closing the circle" *Proc Natl Acad Sci USA*, 1999; 96:8804-6.
Poole et al., "The V proteins of simian virus 5 and other paramyxoviruses inhibit induction of interferon-beta" *Virology*, 2002; 303:33-46.
Price et al., "Single-dose mucosal immunization with a candidate universal influenza vaccine provides rapid protection from virulent H5N1, H3N2 and H1N1 viruses" *PLoS One*, 2010; 5:e13162.
Racaniello et al., "Cloned poliovirus complementary DNA is infectious in mammalian cells" *Science*, 1981; 214(4523):916-9.
Randall et al., "Comparison between parainfluenza virus type 2 and simian virus 5: monoclonal antibodies reveal major antigenic differences" *J Gen Virol*, 1988; 69(Pt 8):2051-60.
Roberts et al., "Vaccination with a recombinant vesicular stomatitis virus expressing an influenza virus hemagglutinin provides complete protection from influenza virus challenge" *J Virol*, 1998; 72:4704-11.
Roberts et al., "Recovery of negative-strand RNA viruses from plasmid DNAs: a positive approach revitalizes a negative field" *Virology*, 1998; 247:1-6.
Roberts et al., "Attenuated Vesicular Stomatitis Viruses as Vaccine Vectors" *J Virol*, 1999; 73(5):3723-32.
Robinson et al., "Protection against a lethal influenza virus challenge by immunization with a haemagglutinin-expressing plasmid DNA" *Vaccine*, 1993; 11(9):957-60.
Robinson et al., "DNA immunization for influenza virus: studies using hemagglutinin- and nucleoprotein-expressing DNAs" *J Infect Dis*, 1997; 176 Suppl 1:S50-5.
Rosenberg et al., "Studies of canine respiratory viruses. I. Experimental infection of dogs with an SV5-like canine parainfluenza agent" *Am J Epidemiol*, 1971; 94(2):147-65.
Ross et al., "C3d enhancement of antibodies to hemagglutinin accelerates protection against influenza virus challenge" *Nat Immunol*, 2000; 1:127-31.
Rott et al., "Influenza viruses, cell enzymes, and pathogenicity" *Am J Respir Crit Care Med*, 1995; 152(4 Pt 2):S16-9.
Rupprecht et al., "Ineffectiveness and comparative pathogenicity of attenuated rabies virus vaccines for the striped skunk (Mephitis mephitis)." *J Wildl Dis*, 1990; 26(1):99-102.
Rupprecht et al., "Human infection due to recombinant vaccinia-rabies glycoprotein virus" *N Engl J Med*, 2001; 345(8):582-6.
Rupprecht et al., "Current and future trends in the prevention, treatment and control of rabies" *Expert Rev Anti Infect Ther*, 2006; 4(6):1021-38.
Sarmento et al., "Rabies virus-induced apoptosis involves caspase-dependent and caspase-independent pathways" *Virus Res*, 2006; 121(2):144-51.
Schmitt et al., "Involvement of the cytoplasmic domain of the hemagglutinin-neuraminidase protein in assembly of the paramyxovirus simian virus 5" *J Virol*, 1999; 73:8703-12.
Schmitt et al., "Requirements for budding of paramyxovirus simian virus 5 virus-like particles" *J Virol*, 2002; 76:3952-64.
Sekaly, "The failed HIV Merck vaccine study: a step back or a launching point for future vaccine development?" *J Exp Med*, 2008; 205(1):7-12.
Singh et al., "A recombinant measles virus expressing hepatitis B virus surface antigen induces humoral immune responses in genetically modified mice" *J Virol*, 1999; 73:4823-8.
Soboleski et al., "Cold-adapted influenza and recombinant adenovirus vaccines induce cross-protective immunity against pH1N1 challenge in mice" *PLoS One*, 2011; 6(7):e21937.
Steel, "New strategies for the development of H5N1 subtype influenza vaccines: progress and challenges" *BioDrugs*, 2011; 25:285-98.
Stephenson et al., "Confronting the avian influenza threat: vaccine development for a potential pandemic" *Lancet Infect Dis*, 2004; 4(8):499-509.

(56) References Cited

OTHER PUBLICATIONS

Strasser et al., "Apoptosis signaling" *Annu Rev Biochem*, 2000; 69:217-45.
Subbarao et al., "Evaluation of a genetically modified reassortant H5N1 influenza A virus vaccine candidate generated by plasmid-based reverse genetics" *Virology*, 2003; 305:192-200.
Suguitan et al., "The multibasic cleavage site of the hemagglutinin of highly pathogenic A/Vietnam/1203/2004 (H5N1) avian influenza virus acts as a virulence factor in a host-specific manner in mammals " *J Virol*, 2012; 86:2706-14.
Sun et al., "Conserved cysteine-rich domain of paramyxovirus simian virus 5 V protein plays an important role in blocking apoptosis" *J Virol*, 2004; 78:5068-78.
Sun et al., "PLK1 down-regulates parainfluenza virus 5 gene expression" *PLoS Pathog*, 2009; 5(7):e1000525.
Sun et al., "Synthesis and biological evaluation of analogues of AKT (protein kinase B) inhibitor-IV" *J Med Chem*, 2011; 54(5):1126-39.
Sun et al., "Identification of a phosphorylation site within the P protein important for mRNA transcription and growth of parainfluenza virus 5" *J Virol*, 2011; 85:8376-85.
Sun et al., "Sumoylation of the P protein at K254 plays an important role in growth of parainfluenza virus 5" *J Virol*, 2011; 85:10261-8.
Takimoto et al., "Recombinant Sendai Virus Expressing the G Glycoprotein of Respiratory Syncytial Virus (RSV) Elicits Immune Protection against RSV" *J Virol*, 2004; 78(11):6043-7.
Taniguchi et al., "Qb DNA-containing hybrid plasmids giving rise to Qb phage formation in the bacterial host" *Nature*, 1978; 274(5668):223-8.
Timani et al., A Single Amino Acid Residue Change in the P Protein of Parainfluenza Virus 5 Elevates Viral Gene Expression *J Virol*, 2008; 82: 9123-33.
Tolson et al., "Immune response in skunks to a vaccinia virus recombinant expressing the rabies virus glycoprotein" *Can J Vet Res*, 1987; 51:363-6.
Tompkins et al., "De novo central nervous system processing of myelin antigen is required for the initiation of experimental autoimmune encephalomyelitis" *J Immunol*, 2002; 168:4173-83.
Tompkins et al., "Matrix protein 2 vaccination and protection against influenza viruses, including subtype H5N1" *Emerg Infect Dis*, 2007; 13:426-35.
Tordo et al., "Canine adenovirus based rabies vaccines" *Dev Biol (Basel)*, 2008; 131:467-76.
Treanor et al., "Safety and immunogenicity of a recombinant hemagglutinin vaccine for H5 influenza in humans" *Vaccine*, 2001; 19(13-14):1732-7.
Treanor et al., "Safety and immunogenicity of an inactivated subvirion influenza A (H5N1) vaccine" *N Engl J Med*, 2006; 354:1343-51.
Tribe "An investigation of the incidence, epidemiology and control of Simian virus 5" *Br J Exp Pathol*, 1966; 47:472-9.
Tsurudome et al., "Extensive antigenic diversity among human parainfluenza type 2 virus isolates and immunological relationships among paramyxoviruses revealed by monoclonal antibodies" *Virology*, 1989; 171(1):38-48.
Tumpey et al., "Mucosal delivery of inactivated influenza vaccine induces B-cell-dependent heterosubtypic cross-protection against lethal influenza A H5N1 virus infection" *J Virol*, 2001; 75:5141-50.
Ulane et al., "Paramyxoviruses SV5 and HPIV2 assemble STAT protein ubiquitin ligase complexes from cellular components" *Virology*, 2002; 304:160-6.
Vandvik et al., "Paramyxovirus SV5 and multiple sclerosis" *Nature*, 1989; 338(6218):769-71.
Vitiello et al., "Immunodominance analysis of CTL responses to influenza PR8 virus reveals two new dominant and subdominant Kb-restricted epitopes" *J Immunol*, 1996; 157(12):5555-62.
Wansley et al., "Naturally occurring substitutions in the P/V gene convert the noncytopathic paramyxovirus simian virus 5 into a virus that induces alpha/beta interferon synthesis and cell death" *J Virol*, 2002; 76:10109-21.
Watabe et al., "Protection against influenza virus challenge by topical application of influenza DNA vaccine" *Vaccine*, 2001; 19(31):4434-44.
Wen et al., "Rabies virus expressing dendritic cell-activating molecules enhances the innate and adaptive immune response to vaccination" *J Virol*, 2011; 85:1634-44.
Weyer et al., "Generation and evaluation of a recombinant modified vaccinia virus Ankara vaccine for rabies" *Vaccine*, 2007; 25(21):4213-22.
Weyer et al., "Poxvirus-vectored vaccines for rabies—a review" *Vaccine*, 2009; 27(51):7198-201.
Whelan et al., "Transcription and replication of nonsegmented negative-strand RNA viruses" *Curr Top Microbiol Immunol*, 2004; 283:61-119.
WHO, "Cumulative Number of Confirmed Human Cases of Avian Influenza A/(H5N1) Reported to WHO" May 31, 2007; Accessed online on Aug. 6, 2015 at apps.who.int/csr/disease/avian_influenza/country/cases_table_2007_05_31/en/index.html#, 1 page.
Wiktor et al., "Protection from rabies by a vaccinia virus recombinant containing the rabies virus glycoprotein gene" *Proc Natl Acad Sci USA*, 1984; 81:7194-8.
Wu et al., "From brain passage to cell adaptation: the road of human rabies vaccine development" *Expert Rev Vaccines*, 2011; 10(11):1597-608.
Xu et al., "Rescue of wild-type mumps virus from a strain associated with recent outbreaks helps to define the role of the SH ORF in the pathogenesis of mumps virus" *Virology*, 2011; 417:126-36.
Young et al., "Clearance of a persistent paramyxovirus infection is mediated by cellular immune responses but not by serum-neutralizing antibody" *J Virol*, 1990; 64(11):5403-11.
Young et al., "Paramyxoviridae use distinct virus-specific mechanisms to circumvent the interferon response" *Virology*, 2000; 269:383-90.
Young et al., "Simian Virus 5 is a Poor Inducer of Chemokine Secretion from Human Lung Epithelial Cells: Identification of Viral Mutants That Activate Interleukin-8 Secretion by Distinct Mechanisms" *J of Virol*, Jun. 2003; 77(12):7124-30.
Zakstelskaya et al., "Persistent SV5 virus infection in continuous cell cultures" *Acta Virol*, 1976; 20(6):506-11.
Zhan et al., "Respiratory syncytial virus (RSV) fusion protein expressed by recombinant Sendai virus elicits B-cell and T-cell responses in cotton rats and confers protection against RSV subtypes A and B" *Vaccine*, 2007; 25(52):8782-93.
Zhang et al., "Comparison of differing cytopathic effects in human airway epithelium of parainfluenza virus 5 (W3A), parainfluenza virus type 3, and respiratory syncytial virus" *Virology*, 2011; 421:67-77.
Zhou et al., "A chimpanzee-origin adenovirus vector expressing the rabies virus glycoprotein as an oral vaccine against inhalation infection with rabies virus" *Mol Ther*, 2006; 14(5):662-72.

Fig. 6
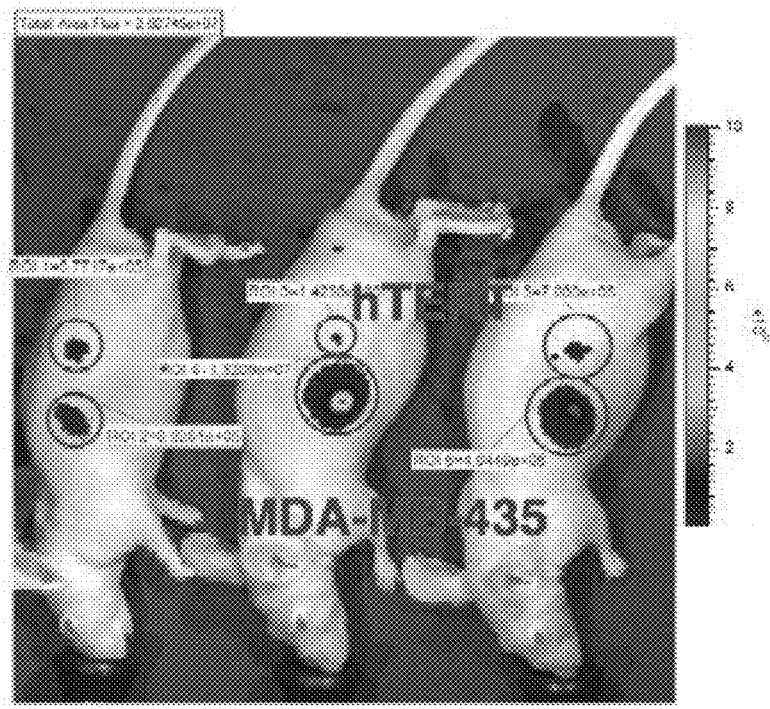
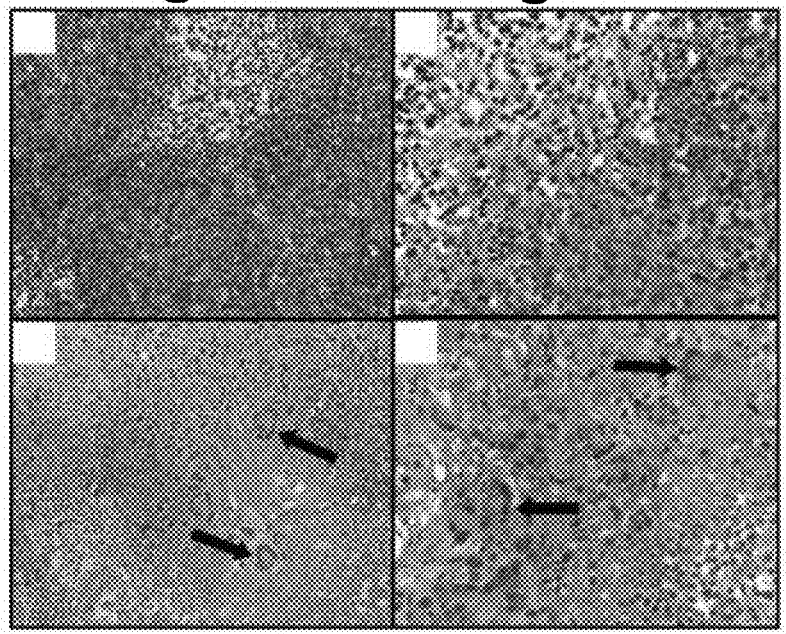
Fig. 7A  Fig. 7B
Fig. 7C  Fig. 7D

PIV5 AS AN ONCOLYTIC AGENT

CONTINUING APPLICATION DATA

This application is a divisional of U.S. National Stage application Ser. No. 14/374,070, filed Jul. 23, 2014, which is the § 371 U.S. National Stage of International Application No. PCT/US2013/022898, filed 24 Jan. 2013, which claims the benefit of U.S. Provisional Applications Ser. Nos. 61/590,056, filed Jan. 24, 2012, 61/590,070, filed Jan. 24, 2012, and 61/683,810, filed Aug. 16, 2012, each of which is incorporated by reference herein.

GOVERNMENT FUNDING

This invention was made with government support under Grant No. R01AI070847 and R56AI081816, awarded by the National Institutes of Health. The Government has certain rights in the invention.

BACKGROUND

Cancer causes significant morbidity and mortality in human populations. Surgery, chemotherapy, and irradiation have been used to treat and control cancers. However, these approaches are not effective against many late stage cancers. In addition, chemotherapy and irradiation often has severe unwanted side effects. For example, it is estimated that over 230,000 new cases of invasive breast cancer will be diagnosed in women in the United States in 2011. Another nearly 40,000 will die from the disease. Breast cancer is second only to lung cancer in causing cancer related deaths in women. This grim outlook seems to contrast the fact that breast cancer detected early is very curable. However, once it metastasizes the cure rate drops precipitously. The standard of care, surgery and chemotherapy, often do not prevent future metastasis even in patients who have been pronounced cured. Thus, there is a need for novel strategies for cancer control, including the treatment of late stage cancers and cancer metastasizes.

SUMMARY OF THE INVENTION

The present invention includes a method of killing a tumor cell, reducing the growth of a tumor cell, reducing tumor size, inducing tumor cells syncytia formation, and/or inducing apoptosis in a tumor cell, the method including infecting the tumor cell with a composition including an isolated a recombinant PIV5 (rPIV5).

The present invention includes a method of killing tumor cells in a subject, the method including administering to the subject an effective amount of a composition including an isolated recombinant parainfluenza virus 5 (PIV5).

The present invention includes a method of treating a subject with a cancer, the method including administering to the subject an effective amount of a composition including an isolated recombinant parainfluenza virus 5 (PIV5).

The present invention includes a method of imaging a tumor in a subject, the method including administering to the subject a recombinant parainfluenza virus 5 (PIV5) expressing a fluorescent polypeptide or detectable agent.

In some embodiments of the methods described herein, the subject is a companion animal. In some embodiments, the companion animal is a dog.

In some embodiments of the methods described herein, the tumor is a primary tumor and/or a metastatic tumor.

In some embodiments of the methods described herein, the tumor is melanoma, basal cell carcinoma, colorectal cancer, pancreatic cancer, breast cancer, prostate cancer, lung cancer (including small-cell lung carcinoma and non-small-cell lung carcinoma, leukemia, lymphoma, sarcoma, ovarian cancer, Kaposi's sarcoma, Hodgkin's lymphoma, Non-Hodgkin's lymphoma, multiple myeloma, neuroblastoma, rhabdomyosarcoma, primary thrombocytosis, primary macroglobulinemia, small-cell lung tumors, primary brain tumors, stomach cancer, head and neck cancers, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, kidney cancer, endometrial cancer, glioblastoma, or adrenal cortical cancer.

In some embodiments of the methods described herein, administration of PIV5 is intratumoral, subcutaneous, intravenous, intranasal, intraperitoneal, intracranial, oral, or in situ.

In some embodiments of the methods described herein, the method further includes administration of an additional therapeutic agent.

In some embodiments of the methods described herein, the PIV5 includes one or more mutations. In some embodiments, a mutation includes a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, and/or a mutation that enhances synctial formation. In some embodiments, a mutation is selected from the group consisting of rPIV5-V/P-CPI–, rPIV5-CPI–, rPIV5-CPI+, rPIV5VΔC, rPIV-Rev, rPIV5-RL, rPIV5-P-S157A, rPIV5-P-S308A, rPIV5-L-A1981D and rPIV5-F-S443P, rPIV5-MDA7, rPIV5ΔSH-CPI–, or rPIV5ΔSH-Rev, and combinations thereof.

In some embodiments of the methods described herein, the PIV5 further includes nucleotide sequences encoding a tumor killing heterologous polypeptide and/or heterologous RNA. In some embodiments, the heterologous polypeptide is MDA7.

The present invention includes an oncolytic agent including a recombinant or mutant parainfluenza virus 5 (PIV5).

In some embodiments, the oncolytic agent includes one or more mutations selected a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, and/or a mutation that enhances synctial formation.

In some embodiments, a mutation includes rPIV5-V/P-CPI–, rPIV5-CPI–, rPIV5-CPI+, rPIV5VΔC, rPIV-Rev, rPIV5-RL, rPIV5-P-S157A, rPIV5-P-S308A, rPIV5-L-A1981D and rPIV5-F-S443P, rPIV5-MDA7, rPIV5ΔSH-CPI–, rPIV5 ΔSH-Rev, or combinations thereof.

In some embodiments, the PIV5 further includes nucleotide sequences encoding a tumor killing polypeptide or RNA. In some embodiments, the heterologous polypeptide is MDA7.

In some embodiments, the oncolytic agent further expresses a fluorescent polypeptide or detectable agent.

The present invention includes compositions including an oncolytic agent as described herein and a pharmaceutically acceptable carrier.

BRIEF DESCRIPTION OF THE FIGURES

FIG. 1A shows infection of MDA-MB-435 cells with PIV5. MDA-MB-435 breast cancer cells in culture were infected with PIV5 at a multiplicity of infection (MOI) of 10. Mock infection consisted of DMED with 1% BSA. The cells were photographed at 2 and 3 days post infection (dpi). FIG. 1B shows growth of PIV5 in the cells. Aliquots of cell culture media were also collected at 0, 48 and 72 hours post infection. Titers of virus in the media were determined using plaque assay.

FIG. 2A shows efficacy of PIV5. Breast cancer cells MDA-MB-435 ($5 \times 10^6$ cells) were injected into 4 to 6-week old nude mice subcutaneously in the right flank. When the volume (length×width$^2$/2) of tumors reached 125 to 175 mm$^3$ on average, PBS or PIV5 at $1 \times 10^6$ plaque forming unit (pfu) viruses were directly injected into the tumors once a week for 5 weeks. The tumor volume was monitored. Shown are the average tumor volumes +/−SD; N=8 for each group. $p \leq 0.005$ for all viruses versus PBS. In FIG. 2B, the experiment was carried out as in FIG. 2A. When the volume (length×width$^2$/2) of tumors reach 125-175 mm$^3$ on average, PBS or PIV5 at $5 \times 10^6$ (High), $5 \times 10^5$ (Med), and $5 \times 10^4$ (Low) plaque forming unit (pfu) were directly injected into tumors once at one week intervals, for 5 weeks. The tumor volume was monitored. N=8 for each group. $p \leq 0.005$ for all viruses vs. PBS.

In FIG. 3A, the weights were measured at 3, 6, 10, 14 and 21 days post injection. The average weight of mice on the day of injection was set as 100 percent. Plotted are the averages of each group +/−S.D. FIG. 3B shows H & E staining of lungs from infected animals at 6 days post infection. Minimal to no inflammation was observed in the sections.

FIG. 4A shows detection of viral RNA in tumors in vivo. The RT-PCR reactions using primers specific for PIV5 genome or mRNA were carried out with tumors collected from the animals. Neg, negative control for RT-PCR; Pos, positive control for RT-PCR. FIG. 4B shows detection of PIV5 in tumors in vivo using a plaque assay. Breast cancer tumors were grown in nude mice as described in the methods section. The tumors were injected with PIV5 ($10^6$ pfu), collected 1, 2, and 6 days post injection, homogenized and directly applied in a plaque assay to determine the titers of viruses. The titer of virus from each individual tumor is graphed. In FIG. 4C, mice with MDA-MB-435 tumors were injected with rPIV5-RL at $6 \times 10^5$ pfu directly in the tumor. 50 µl of the substrate coelenterazine at 400 µg/ml was injected in the tumor at different times after virus injection. All images recorded at same settings: Bin M (4), f1, 2 m, min 5e+04, Max 2e+06. Mouse A is control, which was injected with PBS. Mouse B and C were injected with virus. Tumors in mouse B after virus injection at different times were enlarged.

In FIG. 5A, mice with MDA-MB-435 cells inoculated in two locations (about 15 mm away from each other) developed tumors. The tumor closest to the forelimb was injected with virus. 50 µl of substrate coelenterazine was injected in both tumors on different days and images were recorded. A tumor which developed from MDA-MB-435 (dashed circle, top) was injected with rPIV5-RL ($5 \times 10^5$ pfu). In FIG. 5B, at 1 day post injection, $1 \times 10^6$ MDA-MB-435 cells were injected at about 10 mm away from the tumor in 100 µl volume (dashed circle, bottom). About 4 hours (hrs) later 50 µl of coelenterazine at 400 µg/ml was injected in the tumor at the new inoculation site. Substrate injections were repeated at 3 days post virus injection. These images were recorded using an IVIS camera with the same settings: Bin M (4), f1, 2 m, color bar: min 5e+04, Max 2e+06. Mouse A represents control with PBS injection, mouse B and C represent rPIV5-RL injection.

FIG. 6 shows replication of PIV5 in normal cells vs. cancer cells in vivo. Nude mice were injected with hTERT (top circle) or MDA-MB-435 (bottom circle) cells. The cells were then injected with PBS (left mouse) or rPIV5-RL (middle and right mouse). At 1 day post injection, luciferase expression was measured using an IVIS camera.

FIGS. 7A-7D show the effect of PIV5 on tumors in vivo. Photomicrographs of H&E stained sections of four subcutaneously implanted tumors (cell line MDA-MB-435) illustrating areas of necrosis. FIGS. 7A and 7B are PBS injected tumors (control) at a magnification of 200× and 400× respectively. FIGS. 7C and 7D are PIV5 injected tumors with arrows indicating syncytia formation at a magnification of 200× and 400× respectively.

DETAILED DESCRIPTION OF ILLUSTRATIVE EMBODIMENTS

Figure 1A:
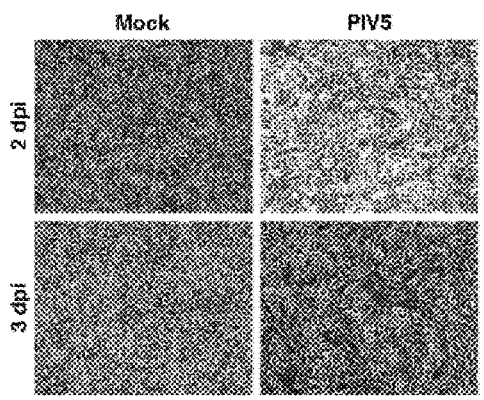
FIGS. 1A and 1B show infection of MDA-MB-435 by PIV5.

Parainfluenza virus 5 (PIV5), a negative-stranded RNA virus, is a member of the *Rubulavirus* genus of the family *Paramyxoviridae* which includes many important human and animal pathogens such as mumps virus, human parainfluenza virus type 2 and type 4, Newcastle disease virus, Sendai virus, HPIV3, measles virus, canine distemper virus, rinderpest virus and respiratory syncytial virus. PIV5 was previously known as simian virus-5 (SV5) (Chatziandreou et al., 2004, *J Gen Virol*; 85:3007-3016). Although PIV5 was originally isolated from cultured primary monkey cells its natural host is the dog in which it causes kennel cough (McCandlish et al., 1978, *Vet Rec;* 102:293-301). Although PIV5 can infect humans (Cohn et al., 1996, *Pathobiology;* 64:131-135), no known symptoms or diseases in humans have been associated with PIV5. Unlike most paramyxoviruses, PIV5 can infect normal cells with little cytopathic effect.

With the present invention, it has been discovered that wild type PIV5 and mutants thereof can function as oncolytic agents, killing a variety of tumor cells, including, but not limited to, breast cancer and melanoma tumor cells. In some aspects, a PIV5 oncolytic agent demonstrates an oncolytic effect only tumor cells and not effecting normal cells. A PIV5 oncolytic agent may demonstrate oncolytic activity against any of a variety of vertebrate cells. Oncolytic activity includes, for example, tumor cell death, reduction of tumor cell growth, reduction in tumor size, the induction of tumor cells syncytia formation, and/or the induction apoptosis in tumor cells. Oncolytic activity may be assayed by any of a variety of known methods, including, but not limited to any of those described in the examples section included herewith.

An oncolytic agent of the present invention includes any of a variety of wild type PIV5 strains, mutant PIV5, or recombinant PIV5 (rPIV5). Wild type strains include, but are not limited to, the PIV5 strains W3A, WR (ATCC® Number VR-288™), canine parainfluenza virus strain 78-238 (ATCC number VR-1573) (Evermann et al., 1980, *J Am Vet Med Assoc;* 177:1132-1134; and Evermann et al., 1981, *Arch Virol;* 68:165-172), canine parainfluenza virus strain D008 (ATCC number VR-399) (Binn et al., 1967, *Proc Soc Exp Biol Med;* 126:140-145), MIL, DEN, LN, MEL, cryptovirus, CPI+, CPI−, H221, 78524, T1 and SER. See, for example, Chatziandreou et al., 2004, J Gen Virol; 85(Pt 10):3007-16; Choppin, 1964, *Virology:* 23:224-233; and Baumgartner et al., 1987, *Intervirology;* 27:218-223. Additionally, PIV5 strains used in commercial kennel cough vaccines, such as, for example, BI, FD, Merck, and Merial vaccines, may be used.

A PIV5 oncolytic agent may be constructed using any of a variety of methods, including, but not limited to, the reverse genetics system described in more detail in He et al. (*Virology;* 237 (2):249-60, 1997).

A PIV5 oncolytic agent may include one, two, three, four, five, or more mutations, including, but not limited to any of those described herein. In some aspects, a combination of two or more (two, three, four, five, six, seven, or more) mutations may be advantageous and may demonstrated enhanced oncolytic activity.

FIG. 1 shows the PIV5 genome structure. PIV5 encodes eight viral proteins. Nucleocapsid protein (NP), phosphoprotein (P) and large RNA polymerase (L) protein are important for transcription and replication of the viral RNA genome. The V protein plays important roles in viral pathogenesis as well as viral RNA synthesis. The fusion (F) protein, a glycoprotein, mediates both cell-to-cell and virus-to-cell fusion in a pH-independent manner that is essential for virus entry into cells. The structures of the F protein have been determined and critical amino acid residues for efficient fusion have been identified. The hemagglutinin-neuraminidase (HN), another viral glycoprotein, is also involved in virus entry and release from the host cells. The matrix (M) protein plays an important role in virus assembly and budding. The hydrophobic (SH) protein is a 44-residue hydrophobic integral membrane protein and is oriented with its N terminus in the cytoplasm. For reviews of the molecular biology of paramyxoviruses see, for example, Whelan et al., 2004, *Curr Top Microbiol Immunol;* 283:61-119; and Lamb & Parks, (2006). *Paramyxoviridae:* the viruses and their replication. In Fields Virology, 5th edn, pp. 1449-1496. Edited by D. M. Knipe & P. M. Howley. Philadelphia, Pa.: Lippincott Williams & Wilkins. An oncolytic agent may have a mutation in one or more of these eight proteins.

PIV5 can infect human (Hsiung et al., 1965, *J Immunol;* 94:67-73), but it has not been associated with any known illness. PIV5 infects mice and hamsters but does not cause any symptoms in the animals. PIV5 can be grown in cells and released to media at a titer up to $8 \times 10^8$ pfu/ml, indicating its potential as a safe gene delivery vector and a possible cost effective way for mass production of the virus.

PIV5 can infect cells productively with little cytopathic effect (CPE) in many cell types. In some cell types, PIV5 infection causes formation of syncytia, i.e., fusion of many cells together, leading to cell death. A mutation may include one or more mutations that promote syncytia formation (see, for example Paterson et al., 2000, *Virology;* 270:17-30).

PIV5 infection does not induce apoptosis (He et al., 2001, *J Virol;* 75:4068-4079. However, recombinant PIV5 lacking SH (rPIV5ΔSH) induces apoptosis in L929 cells through a tumor necrosis factor (TNF)-α mediated extrinsic apoptotic pathway (He et al., 2001, *J Virol;* 75:4068-4079; He et al., 1998, *Virology;* 250:30-40; and Lin et al., 2003, *J Virol;* 77:3371-3383).

The V protein of PIV5 plays a critical role in blocking apoptosis induced by virus. Recombinant PIV5 lacking the conserved cysteine-rich C-terminus (rPIV5VΔC) of the V protein induces apoptosis in a variety of cells through an intrinsic apoptotic pathway, likely initiated through endoplasmic reticulum (ER)-stress (Sun et al., 2004, *J Virol;* 78:5068-5078). Mutant recombinant PIV5 with mutations in the N-terminus of the V/P gene products, such as rPIV5-CPI−, also induce apoptosis (Wansley and Parks, 2002, *J Virol;* 76:10109-10121). A mutation includes, but is not limited to, rPIV5ΔSH, rPIV5-CPI−, rPIV5VΔC, and combinations thereof.

A mutation includes, but is not limited to, a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, and/or a mutation that enhances synctial formation.

A mutation may include, but is not limited to, rPIV5-V/P-CPI−, rPIV5-CPI−, rPIV5-CPI+, rPIV5VΔC, rPIV-Rev, rPIV5-RL, rPIV5-P-S157A, rPIV5-P-S308A, rPIV5-L-A1981D and rPIV5-F-S443P, rPIV5-MDA7, rPIV5ΔSH-CPI−, rPIV5ΔSH-Rev, and combinations thereof.

An oncolytic agent includes a recombinant PIV5 construct including any one or more of the mutations described herein, including one or more of the constructs described the in examples section included herewith.

Also included with the present invention are PIV5 oncolytic agents including heterologous nucleotide sequences. Such a heterologous nucleotide sequence may encode, for example, a heterologous DNA, RNA, or polypeptide. In some aspects, a PIV5 oncolytic agent including heterologous nucleotide sequences may also include one or more of the mutations described herein.

A heterologous nucleotide sequence may be tumor killing agent, for example, a tumor suppressor gene. A tumor suppressor gene is a gene that regulates the growth of cells and, thus, can prevent and inhibit the growth of tumors. A tumor suppressor gene may, for example, slow or stop cell division, repair DNA damage, or regulate cell death via apoptosis. Examples include, but are not limited to, melanoma differentiation-associated gene-7 (MDA-7), p53, BRCA1 (BReast Cancer-1) and BRCA2, ATM (ataxia telangiectasia), retinoblastomia tumor suppressor gene (RB), and TSG101. The melanoma differentiation-associated gene-7 (MDA-7) protein, also known as interleukin (IL)-24, is a tumor suppressor that induces apoptosis in a variety of human malignant cells including lung cancer cells (Ishikawa et al., 2005, Clin Cancer Res; 11:1198-1202).

In some aspects, an oncolytic agent may express a fluorescent polypeptide or detectable agent. Such an agent may be used in diagnostic agents, for examples methods of imaging tumors, including for example, primary tumors and/or metastatic tumors.

Also included in the present invention are compositions including one or more of the viral constructs, as described herein. Such a composition may include a pharmaceutically acceptable carrier. As used, a pharmaceutically acceptable carrier refers to one or more compatible solid or liquid fillers, diluents or encapsulating substances which are suitable for administration to a human or other vertebrate animal. Such a carrier may be pyrogen free. The present invention also includes methods of making and using the oncolytic agents and compositions described herein.

The compositions of the present disclosure may be formulated in pharmaceutical preparations in a variety of forms adapted to the chosen route of administration. One of skill will understand that the composition will vary depending on mode of administration and dosage unit.

The agents of this invention can be administered in a variety of ways, including, but not limited to, intravenous, topical, oral, subcutaneous, intraperitoneal, intramuscular, and intratumor deliver. In some aspects, the agents of the present invention may be formulated for controlled or sustained release. In some aspects, a formulation for controlled or sustained release is suitable for subcutaneous implantation. In some aspects, a formulation for controlled or sustained release includes a patch. An agent may be formulated for enteral administration, for example, formulated as a capsule or tablet.

An oncolytic agent of the present disclosure may be administered to a patient in methods for the treatment of cancer. Cancers to be treated include, but are not limited to, melanoma, basal cell carcinoma, colorectal cancer, pancreatic cancer, breast cancer, prostate cancer, lung cancer (including small-cell lung carcinoma and non-small-cell lung carcinoma), leukemia, lymphoma, sarcoma, ovarian cancer, Kaposi's sarcoma, Hodgkin's lymphoma, Non-Hodgkin's lymphoma, multiple myeloma, neuroblastoma, rhabdomyosarcoma, primary thrombocytosis, primary macroglobulinemia, small-cell lung tumors, primary brain tumors, stomach cancer, head and neck cancers, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, kidney cancer, endometrial cancer, glioblastoma, mesothelioma, oral leukoplakia, Barrett's esophageal cancer, and adrenal cortical cancer. In some aspects, the cancer is a primary cancer. In some aspects, the cancer is metastatic, including, but not limited to a metastatic melanoma, metastatic breast cancer, or metastatic colorectal cancer.

The PIV5 viral constructs described herein are useful as oncolytic agents. The present invention provides methods for killing tumor cells, reducing the growth of tumor cells, reducing tumor size, inducing apoptosis in a tumor cell, and/or inducing tumor cells syncytial formation. The present invention also provides methods for killing tumor cells, reducing the growth of tumor cells, reducing tumor size, inducing apoptosis in a tumor cell, inducing tumor cells syncytia formation, inhibiting tumorigenesis, and/or treating cancer in a subject. This involves administering to a patient an effective amount of an oncolytic agent or composition, as described herein.

The efficacy of such methods for the treatment of cancer may be assessed by any of various parameters well known in the art. This includes, but is not limited to, determinations of a reduction in tumor size, determinations of the inhibition of the growth, spread, invasiveness, vascularization, angiogenesis, and/or metastasis of a tumor, determinations of the inhibition of the growth, spread, invasiveness and/or vascularization of any metastatic lesions, determinations of tumor infiltrations by immune system cells, and/or determinations of an increased delayed type hypersensitivity reaction to tumor antigen. The efficacy of treatment may also be assessed by the determination of a delay in relapse or a delay in tumor progression in the subject or by a determination of survival rate of the subject, for example, an increased survival rate at one or five years post treatment. As used herein, a relapse is the return of a tumor or neoplasm after its apparent cessation.

Several other viruses have been successfully used as oncolytic agents for treating various cancers in animal model systems and some of them are in clinical trials. For example, adenovirus, measles virus (MeV) and Newcastle disease virus (NDV) have are currently being tested in clinical trials. However, the PIV5-based oncolytic agents of the present invention present advantages. While PIV5 is a virus that infects many animals and humans, is not associated with any human diseases. PIV5 causes syncytia formation in tumor cells, leading to cancer cell death. And, as a negative stranded RNA virus, PIV5 is unable to integrate into the host genome.

As used herein "treating" or "treatment" can include therapeutic and/or prophylactic treatments. "Treating a disorder," as used herein, is not intended to be an absolute term. Treatment may lead to an improved prognosis or a reduction in the frequency or severity of symptoms. Desirable effects of treatment include preventing occurrence or recurrence of disease, alleviation of symptoms, and/or diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the invention are only 90, 80, 70, 60, 50, 40, 30, 20, 10, 5 or 1% as frequent or severe as symptoms experienced by an untreated individual with the disorder.

An oncolytic agent may be administered as a composition. Compositions may be administered in any of the methods of the present invention and may be formulated in a variety of forms adapted to the chosen route of administration. The formulations may be conveniently presented in unit dosage form and may be prepared by methods well known in the art of pharmacy. A composition may include a pharmaceutically acceptable carrier. The term "pharmaceutically acceptable," as used herein, means that the compositions or components thereof so described are suitable for use in contact with human skin without undue toxicity, incompatibility, instability, allergic response, and the like. A composition may be a pharmaceutical composition.

Oncolytic agents, as described herein, can be administered by any suitable means including, but not limited to, for example, parenteral (involving piercing the skin or mucous membrane), oral (through the digestive tract), transmucosal, rectal, nasal, topical (including, for example, transdermal, aerosol, buccal and sublingual), or vaginal. Administration may include, for example, subcutaneous, intramuscular, intravenous, intradermal, intraperitoneal, intrasternal, intraarticular injections, intravesical, intra-arteriole, intraventricular, intracranial, intranasal, oral, in situ, intratumoral, by inhalation, or intralesional (for example, by injection into or around a tumor) as well as various infusion techniques.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intraperitoneal, and intratumoral administration. In this connection, sterile aqueous media that can be employed will be known to those of skill in the art. Some variation in dosage will necessarily occur depending on the condition of the subject being treated. The person responsible for administration will, in any event, determine the appropriate dose for the individual subject.

For human and veterinary administration, oncolytic agents, as described herein, may meet sterility, pyrogenicity, and general safety and purity standards as required by the FDA. Such compositions are considered suitable for parenteral or enteral administration to a mammal. Such compositions may be pyrogen-free.

For enteral administration, an agent may be administered in a tablet or capsule, which may be enteric coated, or in a formulation for controlled or sustained release. Many suitable formulations are known, including polymeric or protein microparticles encapsulating drug to be released, ointments, gels, or solutions which can be used topically or locally to administer drug, and even patches, which provide controlled release over a prolonged period of time. These can also take the form of implants. Such an implant may be implanted within the tumor.

Therapeutically effective concentrations and amounts may be determined for each application herein empirically by testing the compounds in known in vitro and in vivo systems, such as those described herein, dosages for humans or other animals may then be extrapolated therefrom.

An agent of the present disclosure may be administered at once, or may be divided into a number of multiple doses to be administered at intervals of time. For example, agents of the invention may be administered repeatedly, e.g., at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that any concentration ranges set forth herein are exemplary only and are not intended to limit the scope or practice of the claimed compositions and methods.

By a "therapeutically effective amount" is meant a sufficient amount of the compound to treat the subject at a reasonable benefit/risk ratio applicable to obtain a desired therapeutic response. It will be understood, however, that the total daily usage of the compounds and compositions of the present invention will be decided by the attending physician within the scope of sound medical judgment. The specific therapeutically effective dose level for any particular patient will depend upon a variety of factors including, for example, the disorder being treated and the severity of the disorder, activity of the specific compound employed, the specific composition employed, the age, body weight, general health, sex and diet of the patient, the time of administration, route of administration, and rate of excretion of the specific compound employed, the duration of the treatment, drugs used in combination or coincidentally with the specific compound employed, and like factors well known in the medical arts.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent. An oncolytic agent as described herein may be used in methods of imaging tumor cells.

An oncolytic agent as described herein may be used in methods of imaging a tumor in a subject. For such applications, an oncolytic agent may express a fluorescent polypeptide or other detectable agent.

An oncolytic agent as described herein may be used for the expression of a heterologous nucleotide sequence or polypeptide sequence within a cell or tumor.

As used herein, the term "subject" represents an organism, including, for example, a mammal. A mammal includes, but is not limited to, a human, a non-human primate, and other non-human vertebrates. A subject may be an "individual," "patient," or "host." Non-human vertebrates include livestock animals (such as, but not limited to, a cow, a horse, a goat, and a pig), a domestic pet or companion animal, such as, but not limited to, a dog or a cat, and laboratory animals. Non-human subjects also include non-human primates as well as rodents, such as, but not limited to, a rat or a mouse. Non-human subjects also include, without limitation, poultry, horses, cows, pigs, goats, dogs, cats, guinea pigs, hamsters, mink, and rabbits.

As used herein "in vitro" is in cell culture and "in vivo" is within the body of a subject. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

In some aspects of the methods of the present invention, a method further includes the administration of one or more additional therapeutic agents. One or more additional therapeutic agents may be administered before, after, and/or coincident to the administration of an oncolytic agent described herein. An oncolytic agent as described herein and additional therapeutic agents may be administered separately or as part of a mixture or cocktail. In some aspects of the present invention, the administration of an oncolytic agent may allow for the effectiveness of a lower dosage of other therapeutic modalities when compared to the administration of the other therapeutic modalities alone, providing relief from the toxicity observed with the administration of higher doses of the other modalities.

As used herein, an additional therapeutic agent may be an agent whose use for the treatment of cancer is known to the skilled artisan. Additional therapeutic treatments include, but are not limited to, surgical resection, radiation therapy, hormone therapy, vaccines, antibody based therapies, whole body irradiation, bone marrow transplantation, peripheral blood stem cell transplantation, the administration of chemotherapeutic agents (also referred to herein as "antineoplastic chemotherapy agent," "antineoplastic agents," or "antineoplastic chemotherapeutic agents"), cytokines, antiviral agents, immune enhancers, tyrosine kinase inhibitors, protein kinase C (PKC) modulator (such as, for example, the PKC activator ingenol 3-angelate (PEP005) or the PKC inhibitor bisindolylmaleimid (enzastaurin), signal transduction inhibitors, antibiotics, antimicrobial agents, a TLR agonist (such as for example, bacterial lipopolysaccharides (LPS) or a CpG oligonucleotide (ODN)), an inhibitor of IDO, such as, for example, 1-MT, and adjuvants.

A chemotherapeutic agent may be, for example, a cytotoxic chemotherapy agent, such as, for example, epidophyllotoxin, procarbazine, mitoxantrone, platinum coordination complexes such as cisplatin and carboplatin, leucovorin, tegafur, paclitaxel, docetaxol, vincristine, vinblastine, methotrexate, cyclophosphamide, gemcitabine, estramustine, carmustine, adriamycin (doxorubicin), etoposide, arsenic trioxide, irinotecan, epothilone derivatives, navelbene, CPT-11, anastrazole, letrazole, capecitabine, reloxafine, ifosamide, and droloxafine.

A chemotherapeutic agent may be, for example, an alkylating agent, such as, for example, irofulven, nitrogen mustards (such as chlorambucil, cyclophosphamide, ifosfamide, mechlorethamine, melphalan, and uracil mustard), aziridines (such as thiotepa), methanesulphonate esters (such as busulfan), nitroso ureas (such as carmustine, lomustine, and streptozocin), platinum complexes (such as cisplatin and carboplatin), and bioreductive alkylators (such as mitomycin, procarbazine, dacarbazine and altretamine), ethylenimine derivatives, alkyl sulfonates, triazenes, pipobroman, temozolomide, triethylene-melamine, and triethylenethiophosphoramine.

A chemotherapeutic agent may be an antimetabolite, such as, for example, a folate antagonist (such as methotrexate and trimetrexate), a pyrimidine antagonist (such as fluorouracil, fluorodeoxyuridine, CB3717, azacitidine, cytarabine, gemcitabine, and floxuridine), a purine antagonist (such as mercaptopurine, 6-thioguanine, fludarabine, and pentostatin), a ribonucleotide reductase inhibitor (such as hydroxyurea), and an adenosine deaminase inhibitor.

A chemotherapeutic agent may be a DNA strand-breakage agent (such as, for example, bleomycin), a topoisomerase II inhibitor (such as, for example, amsacrine, dactinomycin, daunorubicin, idarubicin, mitoxantrone, doxorubicin, etoposide, and teniposide), a DNA minor groove binding agent (such as, for example, plicamydin), a tubulin interactive agent (such as, for example, vincristine, vinblastine, and paclitaxel), a hormonal agent (such as, for example, estrogens, conjugated estrogens, ethinyl estradiol, diethylstilbesterol, chlortrianisen, idenestrol, progestins (such as hydroxyprogesterone caproate, medroxyprogesterone, and megestrol), and androgens (such as testosterone, testosterone propionate, fluoxymesterone, and methyltestosterone)), an adrenal corticosteroid (such as, for example, prednisone, dexamethasone, methylprednisolone, and prednisolone), a leutinizing hormone releasing agent or gonadotropin-releasing hormone antagonist (such as, for example, leuprolide acetate and goserelin acetate), an antihormonal agent (such as, for example, tamoxifen), an antiandrogen agent (such as flutamide), an antiadrenal agent (such as mitotane and aminoglutethimide), and a natural product or derivative thereof (such as, for example, vinca alkaloids, antibiotics, enzymes and epipodophyllotoxins, including, for example vinblastine, vincristine, vindesine, bleomycin, dactinomycin, daunorubicin, doxorubicin, epirubicin, idarubicin, ara-C, paclitaxel, mithramycin, deoxyco-formycin, mitomycin-C, L-asparaginase, and teniposide.

In some aspects of the methods of the present invention, at least one additional therapeutic agent includes radiation therapy. In some aspects, radiation therapy includes localized radiation therapy delivered to the tumor. In some aspects, radiation therapy includes total body irradiation.

Cytokines include, but are not limited to, IL-1α, IL-1β, IL-2, IL-3, IL-4, IL-6, IL-8, IL-9, IL-10, IL-12, IL-13, IL-15, IL-18, IL-19, IL-20, IFN-α, IFN-β, IFN-γ, tumor necrosis factor (TNF), transforming growth factor-β (TGF-β), granulocyte colony stimulating factor (G-CSF), macrophage colony stimulating factor (M-CSF), granulocyte-macrophage colony stimulating factor (GM-CSF), and or Flt-3 ligand. Antibody therapeutics, include, for example, trastuzumab (Herceptin) and antibodies to cytokines, such as IL-10 and TGF-β.

In some aspects of the methods of the present invention, the oncolytic agent administered may include any one or more of the PIV5-based constructs described in International Application No. PCT/US2013/022962, titled "Parainfluenza Virus 5 Based Vaccines," inventor Biao He, filed Jan. 24, 2013, which is hereby incorporated by reference herein in its entirety.

In some aspects of the methods of the present invention, a measurement of response to treatment observed after administering both an oncolytic agent as described herein and the additional therapeutic agent is improved over the same measurement of response to treatment observed after administering either the oncolytic agent or the additional therapeutic agent alone. In some aspects of the methods of the present invention, the administration an oncolytic as described herein and the at least one additional therapeutic agent demonstrate therapeutic synergy. As used herein, a combination may demonstrate therapeutic synergy if it is therapeutically superior to one or other of the constituents used at its optimum dose (Corbett et al., 1982, Cancer Treatment Reports; 66:1187. In some embodiments, a combination demonstrates therapeutic synergy if the efficacy of a combination is characterized as more than additive actions of each constituent.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Example 1

Parainfluenza Virus 5, an Oncolytic Reagent for Breast Cancer

This example demonstrates the ability of PIV5 to prevent the growth of human breast cancer cells in vitro and in vivo in a xenograft model. Live imaging, viral titers and RT-PCR were used to follow the fate of the virus in vivo. PIV5 inhibited the growth of MDA-MB-435 cells in culture and tumors in nude mice. It appeared to do so by causing syncytia formation of tumor cell. When PIV5 was inoculated into a subcutaneously growing tumor, the virus replicated and spread to non-adjacent tumors. The virus was selective; i.e. it did not infect normal, surrounding cells. Furthermore, tail vein injection of high dose of PIV5 did not cause weight loss or illness. Because the PIV5 genome can be modified, it is possible to further enhance its oncolytic activity by changing its genome and by inserting tumor-killing proteins or RNA. Thus, PIV5 is to be considered as a potential oncolytic agent.

Viruses in the Paramyxoviridae family of Mononegavirales are negative stranded, non-segmented RNA viruses (NNSV), including mumps virus (MuV), Newcastle disease virus (NDV) and measles virus (MeV), which are known to be effective in reducing tumors in humans (see, for example, Fielding, 2005, *Rev Med Virol;* 15:135-142; and Myers et al., 2005, *Cancer Gene Ther;* 12:593-599). PIV5, formerly known as simian virus 5 (SV5) (Chatziandreou et al., 2004, *J Gen Virol;* 85:3007-3016), is a member of the *Rubulavirus* genus of the family Paramyxoviridae. Although PIV5 was originally isolated from cultured primary monkey cells its natural host is thought to be the dog in which it causes kennel cough (McCandlish et al., 1978, *Vet Rec;* 102:293-301). PIV5 can infect humans (Cohn et al., 1996, *Pathobiology;* 64:131-135), but with no known symptoms or diseases (Hsiung et al., 1965, *J Immunol;* 94:67-73).

PIV5 has seven genes but encodes eight known viral proteins. Nucleocapsid protein (NP), phosphoprotein (P) and large RNA polymerase (L) protein are important for transcription and replication of the viral RNA genome. The V/P gene of PIV5 is transcribed into both the V mRNA and the P mRNA through the process of "RNA editing." The V mRNA is made when the viral RNA polymerase faithfully transcribes the V/P gene. However, during transcription the viral RNA polymerase complex recognizes a specific RNA sequence in the V/P gene and inserts two non-templated G residues at the site to generate the P mRNA (Thomas et al., 1988, *Cell;* 54:891-902). As a result, the V/P gene is transcribed into two mRNAs at about the same level and translated into two proteins, which share identical N-termini but different C-termini. The V protein plays important roles in viral pathogenesis as well as viral RNA synthesis (Didcock et al., 1999, *J Virol;* 73:9928-9933; Andrejeva et al., 2002, *J Virol;* 76:2159-2167; Poole et al. 2002, *Virology;* 303:33-46; He et al., 2002, *Virology;* 303:15-32; Precious et al., 2005, *J Virol;* 79:13434-13441; Lin and Lamb, 2000, *J Virol;* 74:9152-9166; Lin et al., 2005, *Virology;* 338:270-280; and Lin et al., 2007, *Virology;* 368:262-272).

The fusion (F) protein, a glycoprotein, mediates both cell-to-cell and virus-to-cell fusion in a pH-independent manner that is essential for virus entry into cells. The structures of the F protein have been determined and critical amino acid residues for efficient fusion have been identified (Yin et al., 2006, *Nature;* 439:38-44; and Paterson et al., 2000, *Virology;* 270:17-30). The hemagglutinin-neuraminidase (HN), another glycoprotein, is also involved in virus entry and release from the host cells. The matrix (M) protein is important for virus assembly and budding (Schmitt et al. 1999, *J Virol;* 73:8703-8712; and Schmitt et al., 2002, *J Virol;* 76:3952-3964). The small hydrophobic (SH) protein is an integral membrane protein oriented with its N terminus in the cytoplasm (Hiebert et al., 1988, *J Virol;* 62:2347-2357). Recent work indicates that SH plays a role in blocking TNF-α-mediated apoptosis (Lin et al., 2003, *J Virol;* 77:3371-3383; and Fuentes et al., 2007, *J Virol;* 81:8361-8366).

This example demonstrated that PIV5 was effective as an anti-tumor agent against breast cancer in xenograft model systems and demonstrated similar activity in a melanoma model.

Materials and Methods

Cells and viruses. MDA-MB-435 breast cancer cells (ATCC) and UACC 903 melanoma cancer cells (Trent et al., 1990, *Science;* 247:568-571 and Sharma et al., 2006, *Cancer Res;* 66:8200-8209) were grown in DMEM medium containing 10% FCS. hTERT (human mammary epithelial cells that are immortalized with telomerase (HMEC-hTERT, referred as hTERT) (formerly Clontics, CA, now under Lonza, Basel) cells were grown in MGEM serum-free medium (Lonza). Viruses rPIV5 WT, rPIV5-R-Luc, and rPIV5-CPI– mutant viruses were grown in MDBK cells as described previously (He et al., 1997, *Virology;* 237:249-260). Viruses were titrated in BHK cells using a plaque assay. For in vitro infection, MDA-MB-435 cells were infected at multiplicity of infection (MOI) of 10 in DMEM containing 1% of BSA for 1 hr followed by a medium change to DMEM containing 2% FCS. An aliquot of cell media was collected at 0, 24, 48 and 72 hours post infection (hpi) and the virus titers were determined using a plaque assay.

Animal experiments. All the animal experiments strictly followed the protocols approved by the Institutional Animal Care and Use Committee of The Pennsylvania State University. $5\times10^6$ of MDA-MB-435 cells or $1\times10^6$ of UACC 903 cells in 100 µl PBS were injected subcutaneously into the right flank of 6-8 week old female nude mice. The tumor length and width were measured with a caliper. Tumor volumes were calculated as length×width$^2$/2 (Dethlefsen et al., 1968, *J Natl Cancer Inst;* 40:389-405). When the average tumor volume reached 125-175 mm$^3$, in 3-5 weeks, the mice were grouped by tumors of similar average sizes, and randomly assigned to PBS or PIV5 WT or mutant. Viruses of $10^6$ plaque forming unit (pfu) or PBS (50 µl) were injected directly into the tumor. The injections were repeated weekly. The weight of mice and the volume of tumors were monitored. To determine virus toxicity, WT PIV5 virus ($10^6$ pfu) or PBS was injected through tail vein. Weight and signs of illness were monitored up to 21 days. The mice were sacrificed and lungs, livers, hearts, kidneys, and spleens were collected at 3, 6, 10, 14, and 21 days after virus injection. The organs were fixed in 4% paraformaldehyde and processed for histological analysis, as described below.

RNA isolation from tumors and RT-PCR. Total RNA was isolated using RNA Easy Kit (Qiagen) from tumors collected one week after the last virus injection. For viral RNA amplification, RT-PCR was carried out in one tube of RT-PCR (Gene Choice) following the manufacturer's protocol using PCR primers BH185 and BH186, which hybridize to viral genome and anti-genome respectively. For mRNA RT-PCR, the RT was carried out using poly dT oligo and Superscript II (Invitrogen), and the SS cDNA product was used as template for PCR.

Titration of virus recovered from tumor. Tumors were injected with PIV5-WT virus ($10^6$ pfu in 50 µl volume). At 1, 2, and 6 days post injection, the tumors were collected and homogenized in DMEM. The suspensions were used for plaque assays directly.

Live imaging. To examine the virus amplification and spread in vivo, two tumors were grown 15 mm apart by inoculating MDA-MB-435 cells at two locations in the right flank of a mouse. rPIV5-RLuc of $5\times10^5$ pfu in 50 µl was injected into the tumor close to the forelimb. The luminescence was recorded using IVIS (Xenogen, Inc.) live imaging system on 2, 3, and 25 days post virus injection. For live imaging, mice were anaesthetized with isoflurane, and 400 µg/ml of coelentrazine (made by diluting 1 mg/ml stock in methanol with PBS immediately before injection) was injected locally. To detect spread of virus in vivo, rPIV5-RLuc ($5\times10^5$) were injected directly into the flank tumors of MDA-MB-435 cells. At 1 day post virus injection, $5\times10^6$ MDA-MB-435 cells in 100 µl PBS were injected about 10 mm away from the tumor. Four hours later, 50 µl of 400 µg/ml of the substrate coelenterazine were injected in the tumor and the cell injection site for live imaging recording.

The imaging procedure was repeated at 3 days post virus injection. For virus infection and replication in cancer cells and normal cells in vivo, the mice were inoculated with MDA-MB-435 cells and hTERT cells 10 mm apart on the right flank. The next day, rPIV5-RLuc ($5\times10^5$) or PBS (as negative control) was injected at both cell sites. One day later, live imaging of luminescence was recorded.

Histology analysis. Tumor were collected and fixed with 4% paraformaldehyde in PBS at 4° C. Samples were processed in a Shannon Citadel 2000 paraffin processor (Thermo Fisher) following standard procedures. Processed samples were embedded in paraffin and sectioned at 5 um. The sections were then subjected to H & E staining in a Shandon Gemini Varistainer (Thermo Fisher).

Figure 8:
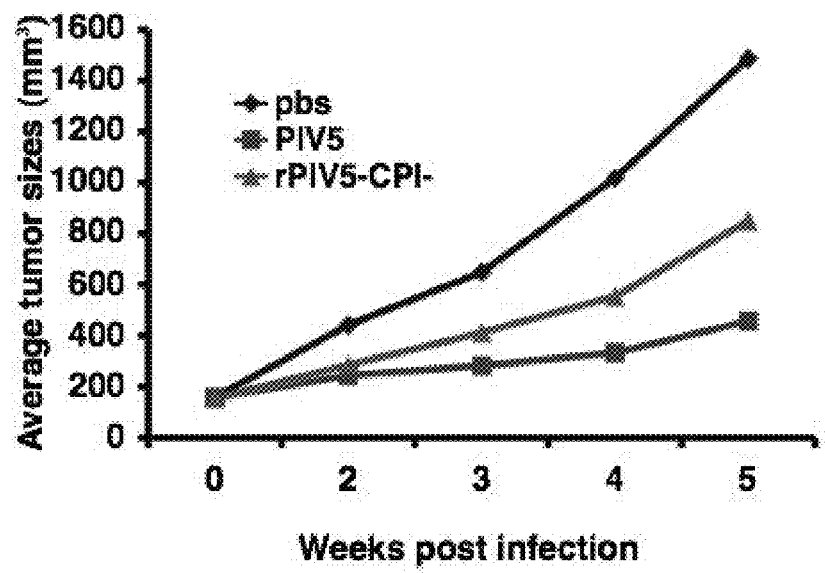
FIG. 8 shows the efficacy of a mutant PIV5 as an oncolytic agent. Breast cancer cells MDA-MB-435 ($5 \times 10^6$ cells) were injected into 6 to 8-week old nude mice subcutaneously. PBS, PIV5 or rPIV5-CPI− at $1 \times 10^6$ plaque forming unit (pfu) viruses were directly injected into tumors once at one week interval. The tumor volume was monitored. Shown are the average tumor volumes =/−SD. N=8 for each group. $p \leq 0.005$ for all viruses vs. PBS.
Figure 9:
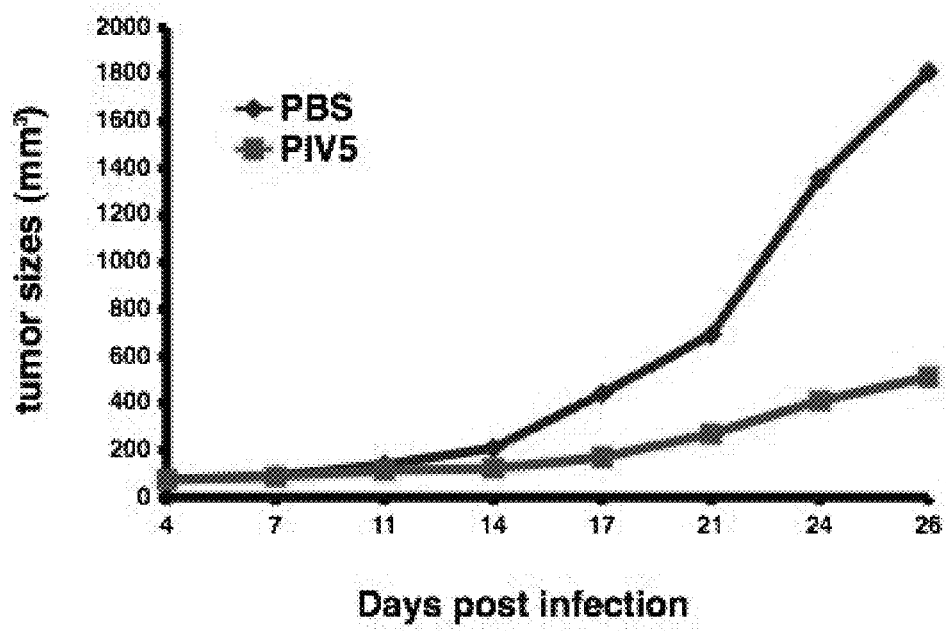
FIG. 9 shows the efficacy of PIV5 as an oncolytic agent in a melanoma model. Melanoma cancer cells UACC 903 ($10^6$ cells) were injected into 6 to 8-week old nude mice subcutaneously. When the volume (length×width$^2$/2) of tumors reached about 100 mm$^3$ on average (about 2 weeks), PBS or PIV5 at $1 \times 10^6$ pfu were directly injected into tumors once at one week interval. The tumor volume was monitored. n=8 for each group. $p \leq 0.005$. Shown are the average tumor volumes =/−SD.

Statistical analysis. Statistical analysis was performed using student's t-test. P values of PIV5 vs. PBS in FIG. 2, FIG. 8 and FIG. 9 are less than 0.05.

Results

Figure 1B:
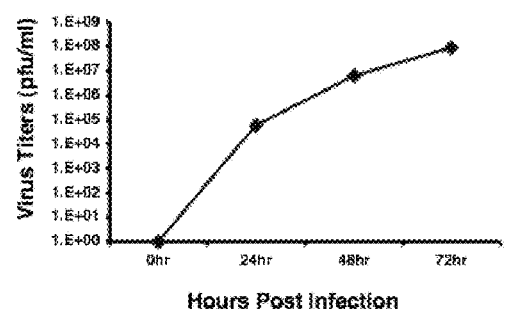

PIV5 infects breast cancer cells. To examine whether PIV5 was a good candidate as an anti-tumor agent, the virus was used to infect a well-studied human metastatic breast cancer cell line, MDA-MB-435, in vitro. PIV5 readily infected MDA-MB-435 cells (FIG. 1A). At three days post infection, the virus grew to a high titer and syncytia were observed in the infected cells (FIG. 1B).

Figure 2A:
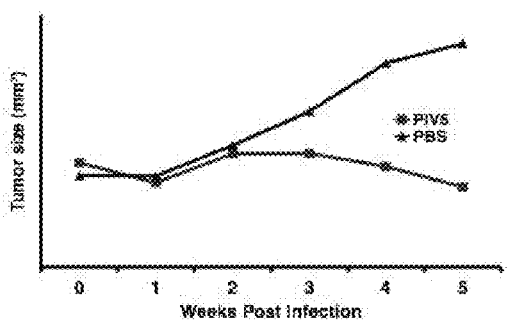
FIGS. 2A and 2B show efficacy of PIV5 as an oncolytic agent in a breast cancer model.
Figure 2B:
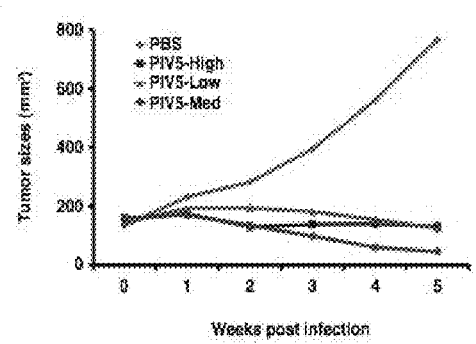

Efficacy of PIV5 as an oncolytic agent against breast cancer in a xenograft mouse model. The efficacy of the wild type virus in killing MDA-MB-435 breast cancer cells grown subcutaneously in the right flank of nude mice was investigated. When the volume of tumors reached 125 to 175 mm$^3$ at about 5-6 weeks, mice were injected with 50 µl PBS or 50 µl wild type PIV5 ($10^6$ plaque forming units (pfu)) in situ, weekly. It was found that PIV5 was effective in reducing tumor growth starting at 3 weeks after the initial injection (FIG. 2A). To further study the effects of PIV5 on tumor growth, a similar experiment was carried out using different doses of viruses. The lowest dose ($5\times10^4$ pfu) was as effective in reducing tumor growth as the highest dose tested ($5\times10^6$ pfu) (FIG. 2B). Interestingly, the tumors disappeared in 8 out of 25 mice injected with PIV5 at the time of experiment termination following the humane endpoint protocol (at 7 weeks after initial injection when the tumors in the PBS group reached 1,000 mm in diameter).

Figure 3A:
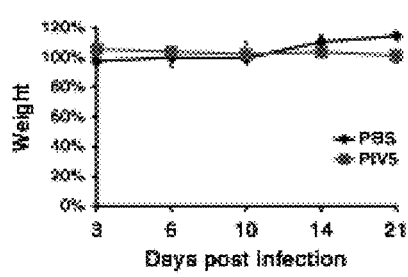
FIGS. 3A and 3B show toxicity of PIV5 in nude mice. Nude mice were injected through the tail vein with PBS, or PIV5 ($10^6$ pfu) (N=12 for each group).
Figure 3B:
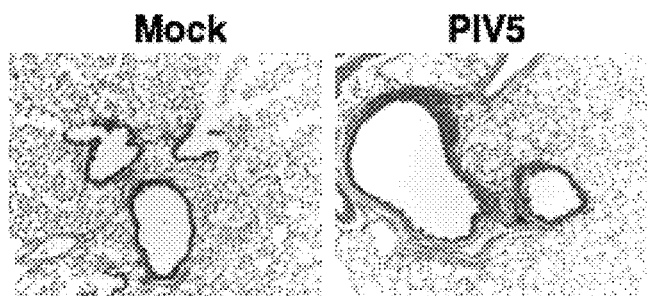

Toxicity of PIV5 in mice. Previously, it was reported that PIV5 infection does not cause disease in immunocompetent mice (Chang and Hsiung, 1965, *J Immunol;* 95:591-601). To evaluate toxicity of PIV5 in nude mice, PBS or PIV5 was injected via tail veins, and monitored the mice for weight loss and signs of illness. Injections of viruses did not cause weight loss or illness up to 21 days post infection (FIG. 3A). Lung, liver, heart, kidney and spleen of the mice were collected at 3, 6, 10, 14 and 21 days after tail vein injections. The organs were sectioned and subjected to H & E staining. A board certified veterinary pathologist found no significant lesions in any of the samples, indicating that PIV5 was safe for immunocompromised mice (FIG. 3B).

Figure 4A:
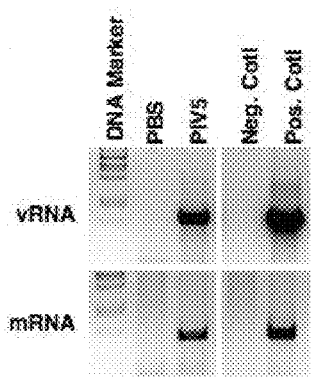
FIGS. 4A-4C show replication of PIV5 in tumors in vivo.
Figure 4B:
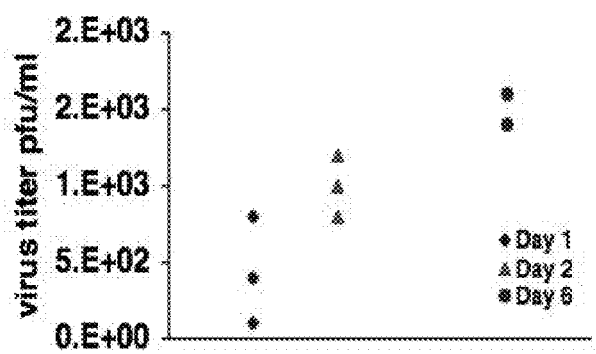

Replication of PIV5 in tumors in vivo. To examine whether the virus replicated in cancer cells in vivo, the tumors were infected with PIV5, collected and assayed for the presence of the viral transcripts and genome using RT-PCR. Viral transcripts and genomes were detected in the tumors at 6 weeks after the initial injection (FIG. 4A), indicating that the virus replicated in the cancer cells in vivo. Because PIV5 is a negative stranded RNA virus, its life cycle does not have a DNA phase, and it is not known to cause latent infection. Hence, detection of viral genomic (negative sense) RNA and mRNA normally indicates virus replication. To further prove that the virus replicated in tumors in vivo, virus titers were directly measured from extracted tumors. Cancer cells were injected into nude mice and about 6 weeks allowed for tumors to develop. PIV5 was then injected into the tumors, and at 1, 2 and 6 days after injection, the tumors were collected and homogenized. Virus titers were measured in the homogenates directly using a plaque assay. We detected virus in tumors at 6 days post infection (dpi) (FIG. 4B). There was an increase in virus titers between 2 dpi and 1 dpi, indicating that the virus had replicated and grown in tumors in vivo. The trend of virus growth continued to 6 dpi, the last point in the experiment, confirming that the virus replicated in tumors in vivo. This result was consistent with the previous findings of viral genome RNA and viral mRNA in tumors extracted from the mice.

Figure 4C:
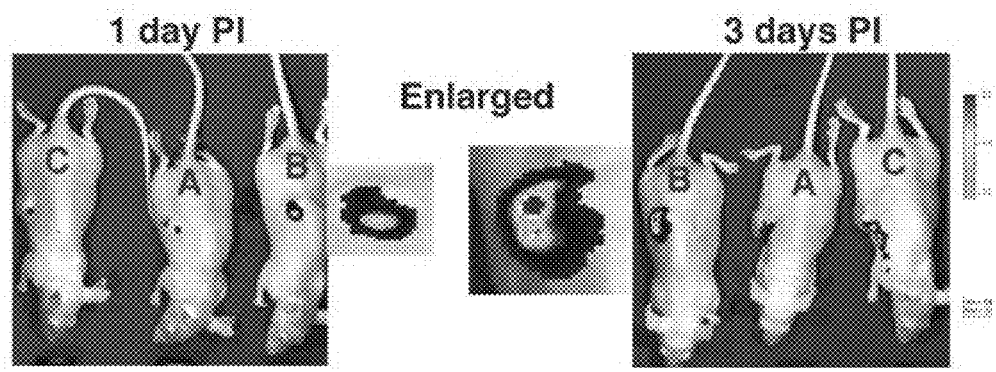

To measure virus replication in tumors in vivo readily and without killing the animals, a recombinant PIV5 was generated that contains renilla luciferase as an extra gene between the HN and L gene (rPIV5-RL). Tumors were injected with rPIV5-RL and 1 and 3 days later, substrate was injected into the tumors directly and expression levels of luciferase in tumors in mice were recorded using the IVIS camera. Luciferase activity was observed in rPIV5-RL-injected tumors, confirming its replication in tumors in vivo in live animals (FIG. 4C). Interestingly, there were increases of the luciferase intensity over time within the same tumor, suggesting that virus might have spread to other cancer cells within the given tumors. No luciferase activity was observed in normal mouse cells, suggesting that rPIV5-RL preferentially infected cancer cells.

Figure 5A:
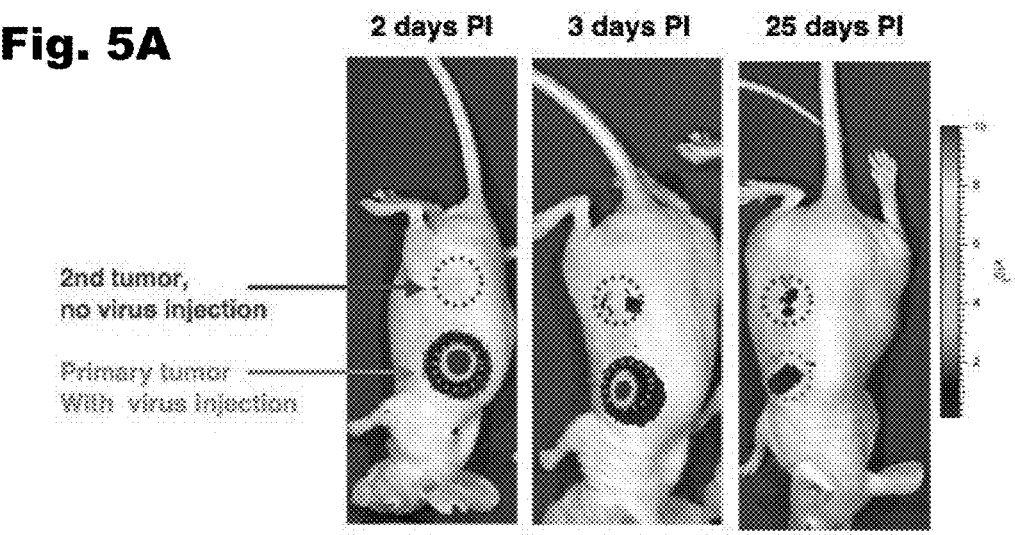
FIGS. 5A and 5B show spread of virus from tumors in vivo.

Spread of PIV5 in tumors in vivo. In order to target metastastic cells, it is critical that the oncolytic virus can spread in vivo. To further test whether PIV5 spread to areas beyond the original injection site, mice with two tumors were used. Virus was injected in one tumor and examined whether there was expression of luciferase in the other tumor. Indeed, expression of luciferase was observed in the tumor that was not injected with virus (FIG. 5A), indicating that PIV5 had spread from the original site of injection to other sites. One potential problem with this experiment was that we were unable to differentiate whether the luciferase activity in the second site was due to virus spread or virus spill during the initial virus injection. It is possible that during the initial injection, some of the virus entered the bloodstream and spread to the other tumor through the blood.

Figure 5B:
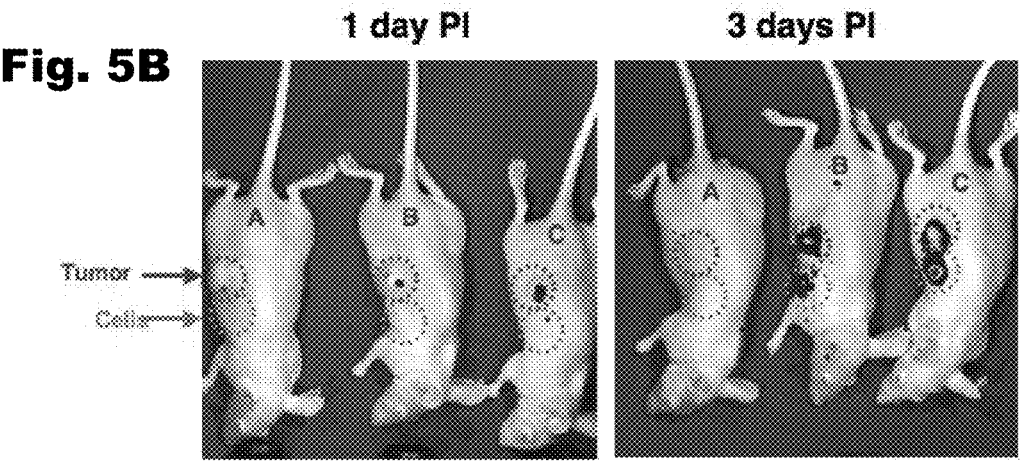

To differentiate between these possibilities, a different injection regimen was used. First virus was injected into tumors as before; waited for 24 hours to allow PIV5 that was not inside cells to dissipate; then injected tumor cells into mice with tumors that had already been injected with PIV5. If virus replication was observed in these newly injected cancer cells, the virus would likely come from other tumors that were injected with virus, indicating that virus spread from tumor cell to tumor cell. Following this new regimen of virus and cells injection, expression of luciferase was observed in newly injected cells (FIG. 5B), indicating that PIV5 spread to other sites in vivo.

Both 5 mm and 10 mm distances between tumors injected with virus and the site of cell injection were used. In both cases, the distant cells expressed luciferase. Thus, PIV5 spread at least 10 mm in vivo. Luciferase activity was only observed in tumor cells, and not in normal mouse cells, strongly suggesting that PIV5 preferentially infected tumor cells in vivo.

Replication of PIV5 in normal cells and cancer cells in vivo. The finding that no luciferase activity was observed in normal cells adjacent to tumors (FIG. 4 and FIG. 5) implied that PIV5 preferentially infected cancer cells in vivo. To further test the preferential infection of cancer cells over normal cells, normal human mammary epithelial cells that are immortalized with telomerase (HMEC-hTERT, referred as hTERT) and MDA-MB-435 cells were infected with PIV5 and virus titers measured. PIV5 grew to $10^7$ to $10^8$ pfu/ml in the cancer cells but grew to $10^5$ to $10^6$ pfu/ml in hTERT, indicating that PIV5 grew much better in the cancer cells. To compare the growth and replication of the virus in vivo, nude mice were injected with equal numbers of hTERT and MDA-MB-435 cells. Three days later, the cells were injected with equal numbers of rPIV5-RL infectious particles. Expression of luciferase was measured one day after infection. rPIV5-RL gave much higher levels of luciferase expression in cancer cells than in normal cells, (FIG. 6) indicating that PIV5 preferentially infected cancer cells in vivo.

Mechanisms of reduction of PIV5 on tumor growth in vivo. To investigate the mechanism of reduction of tumor growth in vivo, tumors were collected after PIV5 or PBS injection. The tumors were fixed, paraffin embedded, sectioned and subjected to H&E staining. While some necroses of cells in the center of tumors were observed in both PIV5 and PBS infected tumors, likely due to insufficient supply of nutrients to sustain rapid tumor growth, formation of syncytia were observed only in PIV5 injected cells, suggesting that PIV5 may kill tumor cells by causing syncytia formation. It appeared that tumor cells were replaced by connective tissue, especially with PIV5 infection (FIG. 7).

Effect of a recombinant PIV5 with mutations in the V/P gene on tumor in vivo. A recombinant PIV5 containing six mutations at the shared N-terminal of V/P proteins of V and P (26, 32, 33, 50 102 and 157) (rPIV5-CPI-) induced cell death and showed accelerated viral gene expression in vitro (Wansley and Parks, 2002, *J Virol;* 76:10109-10121). It was tested for its ability to inhibit tumor growth in nude mice. At about 6 weeks post-inoculation, when tumors grew to about 125 to 175 $mm^3$ in volume, PBS, PIV5 or rPIV5-CPI- were injected into tumors. rPIV5-CPI- reduced tumor growth rate by about 20% compare with PBS (FIG. 8). However, it was not effective as wild type PIV5.

Efficacy of PIV5 against a melanoma model. Because PIV5 was effective in reducing tumor growth in a breast cancer model, whether this oncolytic activity could be detected with other cancers was investigated. Melanoma cancer cells UACC 903 were injected subcutaneously into nude mice and injected PIV5 into the tumors when their average volume was about 100 $mm^3$. PIV5 infection reduced the rate of melanoma growth in vivo, indicating that oncolytic activity of PIV5 extended to melanoma (FIG. 9).

Discussion

This example demonstrated that wild type PIV5 was effective in reducing tumor growth in both breast cancer and melanoma model systems, thus providing a virus as an additional therapeutic agent. Because PIV5 has a non-segmented negative stranded RNA genome, manipulation of the RNA genome directly is not feasible at the present time. However, a reverse genetics system was developed for PIV5, enabling changes in the PIV5 RNA genome through manipulation of its cDNA sequence. Using this system, mutations as well as foreign genes have been introduced into the RNA genome of PIV5 and viable recombinant infectious viruses have been obtained. Thus, it is conceivable that further modification of PIV5 genome will generate more potent oncolytic virus variants. For instance, it has been reported that PIV5 is a good vector for expressing foreign genes (Tompkins et al., 2007, *Virology;* 362:139-150). It is thus possible to express known tumor-specific killing agent such as MDA7 to enhance the killing of tumors in vivo by this oncolytic virus.

Because wt PIV5 did not induce apoptosis in MDA-MB-435 cells, the effective killing of tumors by wt PIV5 in vivo was puzzling. Possibly, PIV5 infection induced an innate immune response in nude mice, resulting in large number of monocytes in the tumors which would lead to cell lysis. However, surprisingly, no abnormal infiltration of immune cells was observed in the tumors. However, syncytia formation in PIV5 infected tumor cells was observed in tissue culture and in tumors collected from animals after injection, suggesting syncytial formation may contribute to the killing of tumors. The oncolytic activity of mutant viruses with various mutations within the PIV5 proteins that enhance syncytial formation will be tested. Such mutants include, but are not limited to, those described by Paterson et al., 2000, *Virology;* 270:17-30.

Previously, a recombinant PIV5 with mutations at the V/P shared region (rPIV5-CPI−) was reported to inhibit tumor growth (Gainey et al., 2008, *J Virol;* 82:9369-9380). This recombinant virus was compared with wild type PIV5 and wild type PIV5 was more effective than rPIV5-CPI− even though rPIV5-CPI− induced a severe cytopathic effect in infected cells compared with wild type PIV5 in tissue culture (Wansley et al., 2003, *Virology;* 316:41-54). It is possible that PIV5 grows better in vivo than rPIV5-CPI−, resulting in a more efficacious inhibition of tumor growth in vivo.

One of the main challenges for using oncolytic virus is that some spread poorly in vivo. This example is the first to demonstrate that PIV5 replicated and spread in tumors in vivo, a characteristic that is essential for treating metastatic tumors, PIV5 appears to be safe in immunodeficient mice since nude mice did not lose weight, show signs of illness or show other pathological effects after tail vein injection with PIV5. The mechanism of this selectivity by an anti-tumor virus is not clear. Interferon signaling plays a role in the selective oncolytic activity (Stojdl et al., 2000, *Nat Med;* 6:821-825; Krishnamurthy et al., 2006, *J Virol;* 80:5145-5155; Obuchi et al., 2003, *J Virol;* 77:8843-8856; and Wollmann et al., 2007, *J Virol;* 81:1479-1491). However, since PIV5 encodes the V protein that abrogates the interferon response, interferon signaling may not play a major role in the selectivity of PIV5.

Recently, it has been reported that AKT, a host serine/threonine plays a critical role in replication of PIV5 (Sun et al., 2008, *J Virol;* 82:105-114). It is thought that AKT1 phosphorylates the P protein of PIV5, an essential co-factor of viral RNA polymerase, and that this phosphorylation is important for the function of the P protein. AKT was first discovered in retrovirus AKT8 as a viral proto-oncogene capable of transforming certain cells (reviewed in Brazil and Hemmings, 2001, *Trends Biochem Sci;* 26:657-664). AKT is a key regulator in the PI3K signaling pathway, and plays an important role in many cellular processes such as cell survival, metabolism, growth, proliferation and mobility. AKT has been found to be activated in many cancers (Redaelli et al. 2006, *Mini Rev Med Chem;* 6:1127-1136; and Yoeli-Lerner and Toker, 2006, *Cell Cycle;* 5:603-605). It has been reported that AKT1 plays a critical role in breast cancer (Ju et al., 2007, *Proc Natl Acad Sci USA;* 104:7438-7443; and Sun et al., 2001, *Am J Pathol;* 159:431-437). Based on the results that AKT, a kinase that plays a critical role in cancer development, also plays a critical role in the replication of PIV5, we hypothesize that AKT activation contributes to the selectivity of PIV5. Further testing of the role of AKT may reveal a novel pathway that is critical for selectivity of oncolytic virus.

PIV5 selectively reduced the size of established tumors of MDA-MB-435 human breast cancer cells and UACC903 human melanoma cells in a mouse xenograft model. This negative strand RNA virus spread within the tumor and to non-adjacent tumors. It did not appear to infect normal mammary epithelial cells and was not toxic to the animal. Thus PIV5 may be developed as an alternative therapy for treatment of late stage and even metastatic breast cancer and other cancers.

Example 2

PIV5 as an Oncolytic Agent

Generation of recombinant PIV5 viruses that induce cell death in cancer cells. To study the functions of the SH protein, a mutant PIV5 virus lacking SH (rPIV5ΔSH) was generated. The mutant virus induces increased expression of TNF-β in infected L929 cells and causes apoptosis. Addition of neutralizing antibody against TNF-β in the media of rPIV5ΔSH-infected L929 cells blocks rPIV5ΔSH-induced apoptosis, indicating TNF-β plays an essential role in rPIV5ΔSH-induced apoptosis. To study the functions of the V protein, a mutant PIV5 lacking the conserved C terminus (rPIV5VΔC) was generated. Infection of rPIV5VΔC induces increased expression of IL-6, IFN-β and enhanced IFN signaling in infected cells. Interestingly, while rPIV5VΔC induces apoptosis in HeLa cells, it does so through an intrinsic apoptotic pathway, independent of IFN. It is thought that rPIV5VΔC induces apoptosis through activation of Erstress initiated intrinsic apoptotic pathway. Mutant PIV5 viruses with mutations in the V/P gene such as rPIV5-CPI− and rPIV5-CPI+ that can also induce apoptosis in cancer cells have been generated. See, for example, He et al., 2001, *J Virol;* 75:4068-4079; He et al., 1998, *Virology;* 250:30-40; Lin et al., 2003, *J Virol;* 77:3371-338; Sun et al., 2004, *J Virol;* 78:5068-5078; Wansley et al., 2003, *Virology;* 316:41-54; Lin et al., 2007, *Virology;* 368(2):262-72; and Timani et al., 2008, *Virol;* 82:9123-9133. In addition, PIV5 mutants with mutations in P and L that induce cell death in infected tumor cells in vitro have been generated.

PIV5 and various mutant PIV5 were used to infect the well-studied human metastatic breast cancer cell line MDA-MB-231, in vitro. These cells were derived from the pleural effusions of patients with metastatic breast cancer (Welch, 1997, *Clin Exp Metastasis;* 15:272-306 and Welch et al., 2000, *Breast Cancer Res;* 2:408-416). PIV5, rPIV5ΔSH, rPIV5VΔC, rPIV5-CPI− and rPIV5-Rev were tested. PIV5 and all PIV5 mutants tested killed the MDA-MB-231 cells, with rPIV5VΔC, rPIV5-CPI− and rPIV5-Rev being most effective. Interestingly, killing of the cells by rPIV5-Rev appears different from the killing by rPIV5VΔC and rPIV5-CPI− as the morphologies of the infected cells look different.

Efficacy of PIV5 mutant as an oncolytic agent against breast cancer in a nude mouse model. As discussed in the previous paragraph, mutant rPIV5-CPI− was effective in killing breast cancer cells MDA-MB-231 in vitro. To test the efficacy of the rPIV5-CPI virus in killing breast cancer cells in vivo, MDA-MB-231 were injected subcutaneously at the right flank of nude mice. Briefly, breast cancer cells MDA-MB-231 ($10^6$ cells) were injected into 4 to 6-week old nude mice subcutaneously. At about 8 weeks after the cancer cell injection, mice were injected with PBS, wild type PIV5 or the rPIV5-CPI- (CPI) in situ. PBS, PIV5 ($10^8$ plaque forming unit, pfu) or rPIV5-CPI- (CPI) ($10^8$ pfu) were directly injected into tumors twice at one week interval. The growth of the tumors was monitored (tumor volume (length×width$^2$/2) was monitored). Tumor growth rate is ratio of tumor volume at 4 weeks after infection to the volume at the first injection. N=8 for each group. The sizes of the tumors at 4 weeks after the injection with rPIV5-CPI- were smaller than that of PBS or wild type PIV5-injected tumors, indicating that the rPIV5-CPI- virus is effective in inhibiting the growth of breast cancer cells in vivo.

Replication of PIV5 in tumors in vivo. To examine whether viruses were replicating in cancer cells in vivo, the tumors were infected with PIV5 and collected. Existence of the virus in the tumor was first investigated using RT-PCR. RT-PCR reactions using primers specific for PIV5 genome or mRNA were carried out using tumors collected from the animals. Viral transcripts and viral genomes were detected in the tumors at 6 weeks after initial injection, indicating the virus was able to replicate in cancer cells in vivo. Because PIV5 is a paramyxovirus, a negative stranded RNA virus, its life cycle does not have a DNA phase, and it is not known to cause latent infection. Hence, detection of viral genomic (negative sense) RNA and mRNA normally indicates virus replication. To further prove that virus replicates in tumors in vivo, virus titers were measured directly from extracted tumors using plaque assay. MDA-MB-231 cells were injected into nude mice and waited for about 6 weeks for tumors to develop. Then, PIV5 was injected into tumors and at 1, 2 and 6 days after injection, tumors collected and the tumor tissues homogenized. Virus titers were measured in the homogenized tissues directly using plaque assay. Virus replication was detected in tumors. Interestingly, there was an increase in virus titers between 2 days post infection (dpi) and 1 dpi, indicating virus indeed replicates and grows in tumors in vivo. The trend of virus growth continues to 6 dpi, the last time point in the experiment, confirming that virus replicates in tumors in vivo. This result is consistent with previous results that viral genome RNA and viral mRNA were detected in tumors extracted from animals. Thus, PIV5 replicates in MDA-MB-231 tumor cells in vivo.

Toxicity of PIV5 in mice. To evaluate toxicity of PIV5 in nude mice, PBS, PIV5 or the rPIV5-CPI- virus were injected into nude mice through tail veins. Briefly, nude mice were injected with PBS, PIV5 ($10^6$ pfu) or rPIV5-CPI- (CPI, $10^6$ pfu) through tail vein (N=12 for each group). The mice were monitored for weight loss and signs of illness. Injections of viruses did not cause weight loss or illness in nude mice up to 21 days post infection. For rPIV5-CPI- virus, the weight was followed up to 10 weeks after injection and no sign of illness or weight loss were found. Lung, liver, heart, kidney and spleen of the mice were collected at 3, 6, 10, 14, 21 days and 10 weeks after tail vein injections. The organs were sectioned and subjected to H & E staining. A board certified veterinary pathologist examined the slides blindly and found no significant lesions in all the samples, indicating PIV5 is safe to the nude mice.

As described in more detail in Example 1, MDA-MB-435 cells, instead of MDA-MB-231 cells, were injected with wild type PIV5 virus. PIV5 is effective in reducing tumor growth in vivo. Interestingly, the lowest dosage used ($5 \times 10^4$ pfu) was as effective as the highest dosage used ($5 \times 10^6$ pfu).

Effect of PIV5 on tumor in vivo. Because wild type (wt) PIV5 does not induce apoptosis in MDA-MB-435 cells, the effective killing of tumors by wt PIV5 in vivo was puzzling. To determine if a PIV5 infection induced massive innate immune responses in nude mice, resulting in large number of lymphocytes in the tumors and the immune responses killed tumors, tumors were collected after PIV5 or PBS injection, sectioned, and subjected to H&E staining. Surprisingly, no abnormal infiltration of immune cells was observed in tumors. While some necrosis of cells in the center of tumors were observed in both PIV5 and PBS infected tumors, likely due to insufficient supply of nutrients to sustain rapid tumor growth, syncytia formations were observed only in PIV5 injected cells, suggesting that PIV5 may kill tumor cells by forming syncytia. It appeared that tumor cells were being replaced by connective tissue, especially in the PIV5 sections.

Examination of PIV5 replication in vivo using live imaging. To measure virus replication in tumors in vivo readily and without killing animals, a recombinant PIV5 that contains renilla luciferase as an extra gene between the HN and L gene (rPIV5-RL) was generated. To examine whether luciferase activity of infected cells reflects rate of virus infection, rPIV5-RL viruses after a series dilution (at factor 2) were used to infect HeLa cells in 96-well plate. At 1 day post infection (dpi), the cells were lysed and processed for renilla luciferase activity according to manufacturer's instruction (Promega Inc., Madison, Wis.). The results indicate that at range of 0.06 to 8 MOI (multiplicity of infectivity, i.e., number of infectious virus per cell), the luciferase activities were in direct correlation with amount of viruses used, indicating the virus can be used as an indicator for examining virus replication quantitatively.

To examine replication of rPIV5-RL in tumors in vivo, the tumors were infected with rPIV5-RL and collected at 1, 3 and 6 days after injection. The tumors were homogenized and used for luciferase assay. Luciferase activity was detected, indicating that PIV5 replicates in tumors in vivo. To examine replication of PIV5 in tumors in vivo without killing the animals, an IVIS camera was used. The tumors were injected with $6 \times 10^5$ plaque-forming units (pfu) of rPIV5-RL. At 1 and 3 days after virus injection, substrate was injected into tumors directly and expression levels of luciferase in tumors in mice were recorded using the IVIS camera. Luciferase activities were observed in rPIV5-RL-injected tumors, confirming that PIV5 replicates in tumors in vivo in live animals. Interestingly, there are increases of the luciferase intensity over time within the same tumor, suggesting that virus may have spread to other cancer cells within the given tumors. Interestingly, no luciferase activity was observed in normal mouse cells, suggesting that rPIV5-RL preferentially.

Spread of PIV5 in tumors in vivo. The ability to spread in vivo is a critical characteristic of any effective oncolytic virus, especially to target metastatic cancer. To further test whether PIV5 can spread to areas beyond the original injection site, mice with two tumors were used. Virus was injected in one tumor and whether there is expression of luciferase in another tumor was examined. Expression of luciferase was observed in the tumor that was not injected with virus, indicating that PIV5 can spread from the original site of injection to other sites. However, this experiment is that we cannot differentiate whether the luciferase activity in the other site is due to virus spread or virus spill during initial virus injection. It is possible that virus was not restricted to the initial injection site during initial virus injection and some entered the bloodstream and spread to the other tumor that was not injected with virus. To differentiate the difference between virus from initial injection and virus produced from the initially injected tumor, a different injection regimen was used. Virus was injected into tumors as before. Then, 24 hours was to pass, to allow PIV5 that is not inside cells to dissipate. Then tumor cells were injected into the mice that have tumors that were already injected with PIV5. If virus replication is observed in these newly injected cells, the virus will likely come from the tumors that are injected with virus, indicating that virus can spread from tumors to other tumor cells. Following the new regimen of virus and cells injection, expression of luciferase was observed in the newly injected cells, indicating that PIV5 spreads to other sites in vivo. Using both 5 mm and 10 mm distance (distance between tumors injected with virus and site of cell injection), it was found that both cells expressed luciferase, indicating that PIV5 can spread at least 10 mm in vivo. Interestingly, luciferase activity was only observed in tumor cells, but not in normal mouse cells, suggesting that PIV5 preferentially infects tumor cells in vivo and/or preferentially replicates in cancer cells over normal cells. The ability to spread within a host is critical for oncolytic virus to be used as an anti-cancer agent. This has been a challenge for adenovirus-based oncolytic virus studies. Examples 1 and 2 indicate that PIV5 spreads in tumors in vivo. PIV5 will be tested against metastasized breast cancer in vivo in Example 3.

Efficacy of PIV5 mutant as an oncolytic agent against lung cancer in a syngeneic mouse model. To investigate whether PIV5 mutants have the potential to reduce the size of solid tumors in an immune competent animal, a tumor model system based on C57BL/6 mouse injected with tumorigenic Lewis lung carcinoma cells (LL2) (Bertram and Janik, 1980, *Cancer Lett;* 11) will be used. To start this study, the killing of the LL2 cells by PIV5 was examined in vitro and it was found that rPIV5-CPI– induces CPE. Briefly, mouse lung cancer cells (LL2) were injected into C57/B16 mice. The tumors developed from the cells were injected with rPIV5-RL, a recombinant PIV5 containing luciferase gene. The tumors from three mice were collected at 1, 2, 3 and 6 days after virus injection and processed for luciferase assay. Then, cells were injected subcutaneously in the right flank of C57/B16 mice. Then PBS, wild type PIV5 and the CPI– virus were injected into the mice through tail veins. Briefly, C57/Black 6 mice were injected with lung cancer cells LL2. PIV5 ($4\times10^6$ pfu), CPI ($4\times10^6$ pfu) or PBS was injected through tail veins of the mice (n=8 for each group) at three days intervals. Tumor growth and weight of mouse were monitored. The experiment was terminated at day 14 after injection of the virus to relieve the pain and suffering of the mice due to the over-growth of the tumors in the control group following the instructions from our IACUC. Tumor size as well as weight was monitored. It was found that the CPI– virus injection reduced the tumor sizes by average about 50% and no differences in the weights of the mice were found.

Thus, testing the oncolytic activity of rPIV5-CPI– in vivo indicates that rPIV5-CPI– is effective in reducing tumor growth in both a nude mouse model and in a C57/B16 mouse model.

Replication of PIV5 in tumors in C57/B16 mice. To investigate whether PIV5 replicates in tumors in vivo, rPIV5-RL was injected into tumors from lung cancer cells in vivo and measured luciferase activity of the tumors at various points after virus injection. Luciferase activity was detected in tumors at 1, 2, 3 and 6 days after injection, indicating that PIV5 replicates in tumors in vivo. An increase of luciferase activity was also observed at day 2, indicating virus growth since viral protein production reaches a peak at 24 hours post infection. Interestingly, luciferase activities were also detected in the spleens of mice even though the virus was injected into tumors directly.

The efficacy of rPIV5VΔC as an oncolytic agent was tested. While PIV5 has oncolytic activity, the rPIV5VΔC mutant construct was tested, to see if oncolytic activity can be enhanced. rPIV5VΔC, a recombinant PIV5 lacking the conserved cysteine rich C terminus of the V protein, induces apoptosis in infected cells (He et al., 2002, *Virology;* 303: 15-32). While average tumor size of PBS-treated group reached 1500 mm$^3$, an upper limit of tumor size allowed by IACUC guideline, average sizes of PIV5 and rPIV5VΔC infected tumors were about 400 mm$^3$ and 200 mm$^3$ respectively in 5 weeks, indicating both viruses are effective against tumor growth in vivo. Interestingly, half of the tumors (4 out of 8) disappeared in rPIV5VΔC-infected group, 1 out of 8 in PIV5 group and none in PBS group. Statistical analysis shows the difference between PIV5 and rPIV5VΔC treatment is statistically significant. Thus, rPIV5VΔC is more effective than PIV5.

Both rPIV5VΔC and rPIV5-CPI– induced cell death on infection of breast cancer cells such MDA-MB-231 and MDA-MB-435 and lung cancer cells such LLC2. Additional PIV5 mutants will be tested to identify mutations and characteristics that will further enhance oncolytic activity of PIV5.

Generation of rPIV5-MDA7 and preliminary testing of rPIV5-MDA7 in vivo. A recombinant PIV5 containing a MDA7 gene between the PIV5 HN and L genes (rPIV5-MDA7) has been produced. RT-PCR was performed to confirm insertion of the MDA7 gene between the HN and L genes in putative rPIV5-MDA7-infected cells using primers specific to the HN and L genes and the resultant RT-PCR fragment sequenced. The sequence from the RT-PCR product match the input cDNA sequence, indicating rPIV5-MDA7 has been obtained.

Briefly, for the testing of rPIV5-MDA7 and rPIV5-Bax, breast cancer tumors were developed as previously described herein. Each tumor received 50 μl of PBS, or a dose of $1\times10^6$ pfu virus in 50 μl volume. Injection was repeated at an interval of one week. N=6 for each group. The tumor sizes (width$^2$×length/2) for PBS and rPIV5-MDA7 injections were between 120-200 mm$^3$. Each tumor received 50 μl of PBS, or a dose of $1\times10^6$ pfu virus. Injection repeated at an interval of one week. N=9 for PBS and rPIV5-MDA7 group; N=6 for rPIV5-Bax. rPIV5-Bax injection dose was $2.5\times10^4$ pfu. At 5 weeks after PBS injection, the PBS group was removed from the experiment because tumors became too large. However, observation of tumors injected with viruses continued. By 8 weeks after virus injection, all tumors disappeared from rPIV5-MDA injection group. $P<0.005$ for all time points between PBS and rPIV5-MDA7.

The rPIV5-MDA7 virus replicates as well as wild type and its efficacy in inhibiting tumor growth has been tested. MDA-MB-435 cells were injected into nude mice and then injected PBS, PIV5 (wild type, wt) or rPIV5-MDA7 into the tumors directly. Amazingly, rPIV5-MDA7 reduced size of tumors dramatically. As described in Example 1, with the mutant rPIV5-CPI virus, inhibition of tumor growth was only observed after injection of a, i.e., the tumors continued to grow after the virus injection but at a slower rate. With rPIV5-MDA7, the size of tumors injected with actually reduced. Not only the actual size of tumor was reduced, dosage of virus that is effective was much lower than before (only $1\times10^6$ pfu of rPIV5-MDA7 vs. $1\times10^8$ pfu of rPIV5-CPI– for each injection). These results have been confirmed.

In addition, a recombinant virus expressing Bax (rPIV5-Bax) has been tested, which is thought to be one of the strongest cell death inducers. Preliminarily, rPIV5-Bax was not as effective as rPIV5-MDA7 even though rPIV5-Bax inhibited tumor growth initially.

Mutants such as rPIV5VΔC and rPIV5-CPI− (or other mutations with increased oncolytic potential) and expression of MDA7 will be combined together to generate a new recombinant PIV5 and to test its efficacy as detailed in Example 4. In addition, a direct comparison of efficacy of rPIV5-MDA7 to AdV-MDA7 (an oncolytic virus that is in clinical trial) will be undertaken.

AKT plays a critical role in replication of PIV5 and other negative stranded RNA viruses. Non-segmented negative stranded RNA viruses such as measles virus (MeV), Newcastle disease virus and vesicular stomatitis virus (VSV) have been used as oncolytic agents and some of them have advanced to clinical trials. However, the underlying reason that causes these viruses to preferentially replicate in cancer cells is not clear. We have found that siRNA and inhibitors against AKT1, a kinase that plays an important role in cancer development, block replication of PIV5 as judged by viral protein expression and virus growth, as well as MeV and VSV. Since AKT is often activated in cancer cells, it is possible that the oncolytic viruses from PIV5, MeV or VSV target cancer cells because of their dependence on AKT for replication, providing an explanation for the selectivity of oncolytic viruses on cancer cells.

A role of AKT1 in phosphorylation of the P protein of PIV5. In the experiments described above, inhibitors were added after virus was incubated with cells, indicating the effect of the inhibitors on the virus life cycle was post-entry. The fact that the siRNA against AKT and the inhibitors against AKT reduce viral protein expression indicates that AKT likely plays a role in viral RNA synthesis. To examine this possibility, a PIV5 mini-genome construct was utilized (Lin et al., 2005, Virology; 338:270-280). AKT inhibitor blocked reporter gene expression from the mini-genome system, indicating that AKT plays a critical role in viral RNA synthesis (Sun et al. 2008, J Virol; 82:105-114). The fact that AKT inhibitor inhibits viral RNA synthesis from the mini-genome system, suggests that AKT likely targets a component of the viral RNA polymerase complex, which is minimally comprised of the P and L proteins for all NNSVs. It is known that the phosphorylation of the P protein plays a critical role in viral RNA synthesis (Lu et al., 2002, J Virol; 76:10776-10784). Since AKT is a protein kinase, the effect of the AKT inhibitor on phosphorylation of P in PIV5-infected cells was examined. The AKT inhibitor reduced phosphorylation of the P protein of PIV5 by about 30% without affecting viral protein translation during the same labeling period. The incomplete inhibition of P phosphorylation by AKT inhibitor is likely due to the fact that P has multiple phosphorylation sites and AKT contributes to phosphorylation of some of the sites (or a single site).

The fact that AKT inhibitor reduces phosphorylation of P indicates AKT plays a role in P phosphorylation. However, it is not clear whether the effect is direct or indirect. To test whether AKT can phosphorylate P directly, PIV5 P protein was purified from bacteria using a His-tagged vision of the P protein using an approach similar to the ones employed to purify large numbers of bacteriophage T7 RNA polymerase (He et al., 1997, Protein Expr Purif 9:142-151). In vitro kinase assays were been carried out and it was demonstrated that AKT1 phosphorylates the recombinant P protein from bacteria. To ensure the protein phosphorylated by AKT is indeed P, not a non-specific bacteria protein co-purified with P and migrated at the same location as the P protein, the recombinant P protein was further immunoprecipitated with P-specific antibody (P282 and Pk) and carried out the in vitro kinase assay. The result confirms that the recombinant P purified from bacteria is phosphorylated by AKT1. These data strongly indicate that AKT phosphorylates P in infected cells directly and this phosphorylation plays a critical role in the function of the P protein. To further explore this, the phosphorylation site of AKT within P will be identified.

Example 3

Phase I/II Clinical Trial of Canine Parainfluenza Virus as an Anti-cancer Agent

Cancer causes significant morbidity and mortality in both dogs and people. Surgery, radiation, and chemotherapy can be used to treat and control some cancers; however, these approaches are often ineffective against late to end stage disease. In addition, removal of tumors is invasive, and radiation and chemotherapy carry risk of severe, unwanted side effects. Safer, more effective treatments are needed.

The use of these viruses as anti-tumor agents is being pursued as an alternative to standard cancer therapies. Many viruses have demonstrated efficacy in killing cancer cells in vitro and in vivo and some are currently being tested in human clinical trials. For example, ONYX-015, an adenovirus derived anti-tumor agent, has been used alone and in combination with chemotherapy in clinical trials for a variety of human cancers. Phase I/II trials of ONYX-015 in treating head and neck cancer have demonstrated that it is safe and effective. PV701, a viral anti-tumor agent developed from Newcastle disease virus (NDV), has been evaluated in human Phase I trials to treat cancer patients with advanced solid tumors including melanoma, and cancers of the head and neck, colon, and pancreas. Initial results are promising, and additional trials sponsored by the National Cancer Institute are ongoing. However, only a few of the many, many known viruses have shown promise in cancer treatment.

The previous examples determined that canine parainfluenza virus (CPI; also known as parainfluenza virus 5 or PIV5) is effective in treating human breast cancer, human melanoma, and human lung cancer using mouse xenograft models. CPI is an RNA virus in the family Paramyxoviridae. As an RNA virus, it is safer for use in cancer patients than DNA viruses (such as adenovirus) because it does not have a DNA phase in its life cycle. As such, using CPI avoids the possible unintended consequences of genetic modifications of the host cell's DNA by viral DNA recombination or insertion. RNA recombination has not yet been reported.

With this example, dogs with naturally occurring cancers will be used to evaluate the safety and overall response rate (ORR) of CPI-WT in tumor-bearing dogs. This study will determine the dose-limiting toxicity, maximally tolerated dosage, and potential efficacy of wild type canine parainfluenza virus (CPI-WT) in dogs with malignant solid tumors. It will also determine the extent of CPI-WT viral shedding from patients following intra-tumoral virus administration. Viral-based therapies, including recombinant viruses expressing tumor killing proteins (e.g. MDA7), will be studies as anti-cancer agents for pets, and eventually people.

Cancer is a leading cause of death in the adult pet population, and malignant solid tumors (MST) encompass a large proportion of cancers diagnosed. Sarcomas, carcinomas, and even some round cell tumors are included in this classification. Although certain types of MST occur more commonly in specific breeds (e.g. histiocytic sarcoma in the Bernese mountain dog and flat-coat retriever), in reality, all dogs are at risk of MST development. Currently available treatment modalities for dogs with MST include surgery, radiation therapy, and chemotherapy. These treatments are invasive, carry risk of morbidity, are costly, and in many cases are palliative, not curative. Thus, search for efficacious and cost-effective therapies is constant.

Comparative oncology is a discipline that merges the study of naturally occurring cancers in pet animals with studies of cancers in people. Pet dogs are practical models because their cancers arise spontaneously, in animals with intact immune systems. Furthermore, many canine cancers more accurately emulate human cancers in etiology, behavior, treatment, and outcome. This example will provide an additional model system for developing novel oncolytic viral therapies for the treatment humans with cancer.

Malignant solid tumors are neoplastic masses of abnormal tissue that exhibit invasion into surrounding normal tissues, and in some cases have high metastatic potential. MST most commonly arises from mesenchymal (sarcomas) or epithelial tissues (carcinomas) and can occur almost anywhere in the body. Treatment, including surgery, radiation, and chemotherapy, is invasive and carries risk of significant toxicity. These treatments are costly, and for many dogs, they do not result in cure.

Canine parainfluenza virus (also known as parainfluenza virus 5 or PIV5 outside of veterinary field) is an RNA virus in the family Paramyxoviridae. As an RNA virus, it is seemingly safer for use in cancer patients than DNA viruses (e.g. adenovirus) because it does not have a DNA phase in its life cycle. As such, using CPI avoids the possible unintended consequences of genetic modifications of the host cell's DNA by viral DNA recombination or insertion. RNA recombination has not yet been reported. CPI can infect many cell types with little cytopathic effect. However, in some cell types, CPI infection causes syncytia formation leading to cell death. The previous examples have demonstrated that CPI infection reduces tumor growth in vivo, likely through syncytia formation.

Although CPI was originally isolated from cultured primary monkey cells, its natural host is the dog. In most dogs, CPI infection causes no overt clinical signs of disease. Furthermore, most dogs have been vaccinated against this virus. When disease occurs, it manifests as an upper respiratory tract infection (sneezing, nasal discharge, and occasionally cough). With supportive care, prognosis is excellent. Based on its safety record, CPI is an attractive oncolytic virus therapy in dogs.

Trial Design

Inclusion Criteria. Dogs with histologically confirmed spontaneous MST amenable to repeated incisional biopsies are eligible for inclusion. Dogs must be otherwise healthy. All owners are required to sign an informed consent form prior to entering his/her dog into the trial.

Treatment, Assessment and Follow-up. To investigate the objective of maximum tolerated dosage and associated treatment toxicity, a conventional 3+3 phase I trial design will be used, enrolling patients in cohorts of 3. The first cohort will be treated at $1 \times 10^8$ pfu, and dosage escalations will occur in $1 \times 10^1$ pfu increments. All toxicities will be defined using the Veterinary Co-operative Oncology Group Common Terminology Criteria for Adverse Events (VCOG-CTCAE) v1.1. Unacceptable grade of toxicity will be dependent upon category of toxicity experienced. If unacceptable toxicity occurs in one of the three dogs in any cohort, an additional three dogs will be enrolled in that cohort. The goal will be to establish the maximum tolerated dosage (the dosage at which approximately 33% of patients experience unacceptable toxicity) after treating at least 6 dogs in the cohort where toxicity occurs. Overall patient health and occurrence of adverse events will be assessed by patient history and physical examination prior to treatment and at each visit. A complete blood count, serum biochemical profile, and urinalysis will be performed prior to the first treatment and will be repeated prior to the 4th treatment and one month after treatment completion.

A maximum tolerated dosage may not become evident for virus-based therapies as it does for traditional cytotoxic chemotherapeutics. If so, patient accrual could continue indefinitely. Therefore, as an additional endpoint, tumor responses will be evaluated via primary tumor measurements. Antitumor responses will be assessed according to Response Evaluation Criteria in Solid Tumors (RECIST). The longest diameter of the tumor is recorded and evaluated at each examination. Complete response (CR) is defined as disappearance of the tumor or all measurable lesions. Partial response (PR) is defined as at least a 30% decrease in the longest diameter of the tumor or the sum of the longest diameters of the measurable lesions. Progressive disease (PD) is defined as a 20% increase in the longest diameter of the tumor or the sum of the longest diameters of the measurable lesions or the appearance of new lesions. Stable disease (SD) is defined as insufficient shrinkage to qualify for PR and an insufficient increase to qualify as PD. Overall response rate (ORR) will include patients experiencing CR or PR. The intent will be to administer four weekly doses of virus to each dog in the study.

The calculated dose will be prepared in a volume of 0.5 to 1.0 mL. Virus will be administered intratumorally into four quadrants of the tumor. Tumor biopsies will be performed prior to treatments #1 and #4, as well as 4 weeks after treatment completion. Biopsies will be evaluated histopathologically for evidence of regression and to confirm viral infection in tumor.

Assessment of CPI-WT Shedding. Nasal swabs and fecal and blood samples will be collected from dogs prior to treatment initiation, at the time of each weekly treatment, and 2 and 4 weeks following treatment completion. Samples will first be analyzed using RT-PCR. If viral RNA is detected, the numbers of live virus in the samples will be determined.

For this phase I trial design, no special statistical calculations are required. The target enrollment for response assessment is determined using the Simon Minimax design, with a rule-out response probability of 5%, a minimum useful response probability of 25%, an α of 0.05 and a β of 0.10. Based on this design, 15 dogs will be enrolled in the first stage of this trial. If no responses are seen in the first 15 patients entered, the trial may be terminated. If a promising response rate is noted, 5 additional dogs will be enrolled with residual funding of this proposal, and the trial will be continued as part of a competitive renewal proposal.

Because most dogs have been vaccinated against CPI, immunity to CPI may pose a problem. As demonstrated in the other examples included herewith, CPI-positive dogs have been successfully immunized against influenza virus using a CPI-based vaccine. Based on these results, CPI will likely infect solid tumors in previously vaccinated dogs as well.

This is the first oncolytic virus clinical trial in dogs, and it will provide valuable information about the safety and efficacy of CPI-based cancer therapy as an alternative to current cancer treatments. Based on the previous examples, it is expected that the intra-tumoral administration of CPI will be safe and will reduce the size of tumors. Furthermore, significant viral shedding from intra-tumorally treated dogs is not expected, as virus was not detected in nasal swabs of dogs infected intranasally or intramuscularly with this respiratory virus.

The studies described above will be repeated with mutant viral construct, such as a PIV5 viral construct altered to incorporate tumor killing genes such as MDA-7, potentially boosting efficacy. Additionally, these virus-based can be incorporated into other cancer treatment protocols, in hopes of improving tumor control, extending survival times, and possibly improving quality of life. Alternatively, virus-based treatments can be used as a sole modality in cases where other treatments are not viable options.

Success of the proposed experiments will not only lead to a novel therapy for dogs with cancer, but also will move the oncolytic virus field forward. If dogs with spontaneous tumors are established as a suitable model for human cancer treatment with oncolytic viruses, more research will likely be performed, thereby potentially leading to more cancer treatment options for dogs and people.

Five client-owned dogs with either melanoma or sarcoma have been tested. Injections of $1.6 \times 10^8$ pfu to $3.2 \times 10^8$ pfu PIV5 have been well-tolerated by the dogs. No clinical illness has been observed to associate with the injections, indicating that PIV5 injection is safe in dogs.

Example 4

Infection of Dogs with Prior Exposure to PIV5

Infection of "naive" dogs with PIV5 and rPIV5-H3. Dogs were inoculated with rPIV5-H3 via intranasal route, and determined replication of virus in dogs and measured immune responses to the virus. Dogs are routinely vaccinated with vaccines containing live PIV5 at a young age (as early as 3-week old). Through an arrangement with the animal vendor, 8 dogs at 12-week of age without vaccination of live PIV5 were obtained. The titers of PIV5 antibodies in these dogs were determined using ELISA and neutralization assay. All dogs were positive to PIV5 in ELISA. However, neutralization antibody (nAb) titers were undetectable. The dogs (n=4) were infected with PIV5 or rPIV5-H3 via intranasal (IN) route. At 3 and 5 days post infection, nasal swabs were taken from infected dogs, and assayed for existence of viruses. While no virus was detected when the swabs were analyzed using plaque assay, RT-PCR products were detected in 7 of 8 dogs at 3 days post infection (dpi) and very weak RT-PCR signals were detected in 5 of 8 dogs at 5 dpi, suggesting that limited replication of PIV5 in naris of infected dogs at 3 days post-infection and the infection was being cleared at 5 days post-infection. The dogs were bled at 21 days post infection. Increases in anti-PIV5 titers were detected in all dogs, suggesting that the dogs were infected. Measurement of anti-HA titers using HAI assay indicated that all rPIV5-H3 inoculated dogs seroconverted and had HAI titers at average 42.5 (range from 20 to 80) at 3-week post-infection. No HAI was detected in dogs-inoculated with PIV5.

Infection of dogs with exposure to PIV5 with PIV5-HA. To examine whether dogs with prior exposure with PIV5 can still be vaccinated with recombinant PIV5-based vaccines, dogs were obtained that were vaccinated against PIV5 multiple times and had anti-PIV5 neutralizing antibodies. The dogs were infected with rPIV5-H3 via IN route. No virus was detected using plaque assay at 3 and 5 dpi in naris of infected dogs. One out of eight dogs tested positive using RT-PCR at 3 dpi. Dogs were then bled at 3 weeks post-infection. The dogs vaccinated with rPIV5-H3 had HAI titers ranging from 40 to 80 (average 77, 1 at 40 and 5 at 80), indicating that rPIV5-H3 vaccination generated immunity against influenza virus (a 4-fold increase of HAI titer or a HAI titer of 40 is considered protective against influenza virus infection). The nAb titers against PIV5 also increased in rPIV5-H3-infected dogs, confirming the infection of the dogs with rPIV5-H3.

The nAb titers against PIV5 in vaccinated dogs were higher than the "naive" dogs and were as high as 300 (FIG. 14B). All dogs with nAb against PIV5 seroconverted after a single dose IN inoculation of rPIV5-H3, and the titers of anti-H3 antibody had no correlation to the nAb titters against PIV5, further confirming that nAbs of PIV5 had no predictive value in determining immune responses to a PIV5-based vaccine in dogs. The highest titer of nAb against PIV5 in humans is 60, lower than the titers of nAb against PIV5 in dogs. Thus, neutralizing antibody against PIV5 in humans will likely not prevent PIV5-based vaccine candidates from generating protective immunity.

This Example has published as Chen et al., "Evaluating a Parainfluenza Virus 5-Based Vaccine in a Host with Pre-Existing Immunity against Parainfluenza Virus 5," *PLoS One;* 2012;7 (11):e50144, doi: 10.1371/journal.pone.0050144, Epub 2012 Nov. 20, which is incorporated by reference herein in its entirety.

Example 5

PIV5 Mutants as Anti-tumor Agents for Metastatic Breast Cancer

The previous examples demonstrate the oncolytic activity of PIV5 and PIV5 mutants, showing that PIV5 has oncolytic activities against solid tumors in a breast cancer model using nude mice, a melanoma cancer model and a lung cancer model using C57/B16 mice. Importantly, these previous examples also demonstrated that PIV5 can spread from cancer cells to cancer cells in vivo. This example will continue to test PIV5 as an oncolytic agent against metastatic cancer.

PIV5 WT, rPIV5-CPI− and additional mutant PIV5 virus mutants will be tested, following procedures described the previous examples, in the nude mice models including solid tumor model and metastatic model as well as in an immune competent lung cancer model. The following will be tested:

PIV5-WT;

rPIV5-CPI— (Wansley and Parks, 2002, *J Virol;* 76:10109-10121; and Timani et al., 2008, *Virol;* 82:9123-9133), having Y26H, T32I, V33I, L50P, L102P and S157F mutations of the V/P gene;

rPIV5-CPI+ (Wansley and Parks, 2002, *J Virol;* 76:10109-10121; and Timani et al., 2008, *Virol;* 82:9123-9133), having T32I, V33I and S157F mutations of the V/P gene and demonstrating phenotypic properties of induction of CPE and apoptosis;

rPIV5-Rev, having a S1561 mutation of the V/P gene and demonstrating phenotypic properties of induction of CPE and apoptosis;

rPIV5ΔSH (Lin et al., 2003, *J Virol;* 77:3371-3383), having a deletion of the SH gene and demonstrating phenotypic properties of induction of CPE and apoptosis;

rPIV5-P-S157A, having a S157A mutation of the V/P gene and demonstrating phenotypic properties of induction of CPE and apoptosis;

rPIV5-P-S308A, having a S308A of the P gene and demonstrating phenotypic properties of induction of CPE and apoptosis;

rPIV5-L-A1981D, having A1981D mutation of the L gene and demonstrating the phenotypic property of induction of CPE; and rPIV5-F-5443P (Paterson et al., 2000, Virology; 270:17-30), having a S443P mutation of the F gene and demonstrating the phenotypic property of induction of massive syncytia formation.

Further experiments will combine effective mutations within the PIV5 genome and test its efficacy in vivo.

Testing efficacies of PIV5 mutants against solid tumors. The breast cancer model system in nude mice will be used to examine the effects of the additional oncolytic virus candidates such as rPIV5ΔSH, rPIV5-CPI+, rPIV5-Rev, rPIV5ΔC, rPIV5-P-5157A, rPIV5-P-5308A, rPIV5-L-A1981D and rPIV5-F-5443P on tumor growth in vivo. Recent studies of functions of the P protein show that mutating S157 of P to A or S308 to A results in a recombinant virus that induces cell death. Also, a mutation in the L gene of PIV5 (rPIV5-L-A1981D) has been identified that causes cell death. These cell death inducing mutants will likely enhance oncolytic activity of PIV5. It has been reported before that mutation of S to P at 443 position of the F protein causes the F protein to be more effective in promoting cell-to cell fusion (Paterson et al., 2000, *Virology;* 270:17-30). rPIV5-F-S443P, a recombinant virus promotes rapid syncytia formation, may be more effective as an oncolytic virus comparing to wild type PIV5.

Metastatic breast cancer cells MDA-MB-435 (Morales et al., 1999, *Nat Genet;* 21:115-118; and Yang et al., 1999, *J Biol Chem;* 274:26141-26148) cells will be used. The cells will be grown in culture to subconfluence, released from the plate and concentrated to about $5\times10^5$ cells in 200 μl of PBS for injection. For studies of the effects of virus on solid tumors, the cells will be injected into the right supra scapular area of 5-6 week old female athymic mice subcutaneously in a group of 8-10 mice for each virus following well established procedures (Welch, 1997, *Clin Exp Metastasis;* 15:272-306). The development of tumor will be monitored by measuring the mean tumor diameter (the square root of the product of two orthogonal measurements). The tumors will also be examined by histology to determine the status of the tumor cells and the surrounding mammary tissue. Tumors usually become visible by about 2 weeks and will be fully developed in 4-5 weeks when the average of the size of tumors is about 7 mm by 7 mm. At that time, equal numbers ($10^6$ plaque forming unit, pfu) of purified PIV5 wild type, rPIV5ΔSH, rPIV5VΔC, rPIV5-CPI−, rPIV5-Rev rPIV5-P-S157A, rPIV5-P-S308A, rPIV5-LA1981D or rPIV5-F-5443P in 50 μl of PBS or PBS will be injected into the tumor directly. Animals will be monitored and the sizes of the tumors will be measured daily after administration of the virus. Distressed animals will be sacrificed. The experiment will be terminated by about 60 days or sooner before the tumors reach 1.5 centimeter. If one specific mutant virus is found to be more effective in reducing tumor growth, a serial dilution of input virus will be used to determine the lowest dosage that is effective in reducing tumor growth efficiently.

Testing efficacies of PIV5 mutants against metastatic cancer. In order to study the effects of the virus on metastasis the cancer cells (for example, MDA-435GFP, previously described) will be injected into the tail vein of mice with about $5\times10^5$ metastatic breast cancer cells in 100 μl of PBS. The animals will be monitored daily for the presence of palpable tumors. Distressed animals will be sacrificed. After 3 weeks when animal normally develop metastatic cancer, the animals will be examined for the presence of tumors in the lungs and lymph nodes and wild type PIV5, PIV5 mutants in 100 μl of PBS or PBS will also be injected into the mice intravenously. The experiment will be terminated by about 60 days or sooner when animals appear severely distressed.

If the virus has an effect on soft tissue metastatic, it will be determined if the virus affects metastasis to bone. This will be done by inoculation of the cancer cells (about $2\text{-}3\times10^5$ cells in 200 μl PBS, MDA-435GFP) into the left ventricle of the heart of athymic mice. This procedure leads to visible bone osteolysis in about 4-5 weeks after inoculation. Then wild type PIV5, PIV5 mutants in 200 μl PBS or PBS alone will be injected into the animals intravenously. After 4 weeks the femurs will be removed, fixed, decalcified, embedded and sectioned. The sections will be stained with H&E for visualization of the cancer cells and for condition of the bone as described before (Phadke et al., 2006, *Clin Cancer Res;* 12:1431-1440; Mastro et al., 2003, *Clin Exp Metastasis;* 20:275-284; Mastro et al., 2004, *J Cell Biochem;* 91:265-276; and Harms et al., 2004, *Clin Exp Metastasis;* 21:119-128).

Bio-distribution of virus and tumor biology. Metastasis of the tumors and localization of virus in vivo will be examined at 3, 7 and 14 days post infections. Initially, rPIV5-RL will be used to monitor distribution of PIV5 within mice. For PIV5 without luciferase gene, three mice will be sacrificed and organs including lung, liver, kidney, heart and brains collected. The collected organs will be frozen in −80-degree methyl butane and sectioned sagittally at 16 μm on a cryostat. The sections will be fixed with acetone, washed with PBS and then blocked in 3% normal goat serum in PBS for 30 minutes. To study metastasis of the cancer cells, antibody against GFP will be used to incubate with sectioned organ slides; to study localization of the virus, expression of PIV5 virus proteins will be used as an indicator. Appropriate secondary antibodies labeled with fluorescence materials such as PE or Texas Red will be used to incubate with the sections and results will be examined using a confocal microscope as described before (Rubin et al., 2003, *J Virol;* 77:11616-11624).

Virus titers in organs including lung, liver, kidney and brain will be examined. At 3, 7 and 14 days post incubation with viruses, 3 mice will be sacrificed and the organs will be collected. The organs will be weighed and homogenized. Titers of viruses will be determined using plaque assays as described in He et al. (He et al., 1997, *Virology;* 237:249-260).

To study pathology and metastasis of the tumors, major organs including lung, heart, kidney, liver and brain of the mice will be collected at the time of experiment termination. Part of the samples will be sectioned and analyzed as described above. Part of the organs will be subjected to pathology studies.

To investigate mechanism of oncolytic activity of PIV5 mutants and to make PIV5 more efficient in reducing tumor growth in vivo, tumor biology after virus infection will be examined, as described earlier. Tumors will be harvested, sectioned, stained and examined by a veterinarian with training in rodent pathology. Tumor type and progression will be assessed including differentiation, presence of mitotic figures, necrosis, vascularity, and the presence or absence of inflammatory infiltrates and apoptotic bodies.

Since PIV5 causes syncytia in tumors, it is expected that tumors infected with PIV5 mutants will also show syncytia.

For mutants that induce cell death, apoptotic cancer cells will also likely be observed in tumors infected with the viruses. In tumor sections from a pilot study, necrosis was present in both control and PIV5 infected sections, although more pronounced in the PIV5 sections. There was minimal inflammatory response, and no appreciable angiogenesis in any of the sections. Fibrosis and loose connective tissue were more prevalent in the PIV5 infected sections, and syncytia were noted in 2 of 3 PIV5 infected sections and 0 of 3 control sections.

It is possible that single mutations of PIV5 will not be effective in killing metastatic breast cancer in vivo. A recombinant PIV5 with a combination of different mutations of PIV5 such as rPIV5ΔSH-CPI–, or rPIV5ΔSH-Rev will then be generated and tested using the same experimental regiment. The V protein of PIV5 plays an important role in evading host innate immune responses by causing degradation of STAT1, a key regulator of IFN signaling pathway. Interestingly, mutations in the V protein of rPIV5-CPI– render the V protein ineffective in blocking IFN signaling (Wansley et al., 2005, *Virology;* 335:131-144; and Chatziandreou et al., 2002, *Virology;* 293:234-242). It has been reported that rPIV5-CPI– replicates preferentially in cancer cells over normal cells in the presence of interferon, likely due to possible defective IFN signaling pathways often associated with cancer cells (Obuchi et al., 2003, *J Virol;* 77:8843-8856). The sensitivity of the virus to IFN can provide additional selectivity for oncolytic virus. Similarly, rPIV5VΔC, which induces production of IFN-β and is unable to block IFN signaling, may provide additional selectivity for oncolytic virus. Thus, incorporating these mutations (CPI– and/or VΔC of the V protein) will likely increase selectivity of the oncolytic virus. If a recombinant PIV5 with a combination of different mutations is determined to be more effective, a luciferase gene can be inserted into the genome of this virus for bio-distribution study.

C57/B16/3LL model. To examine whether the viruses can kill tumors in an immune competent animal model system, the viruses will be injected into C57BL/6 mice carrying solid tumors generated from Lewis lung carcinoma cells (Bertram and Janik, 1980, Cancer Lett; 11:63-73). To obtain C57BL/6 mice with solid tumors, LL2 cells ($5 \times 10^5$ cells) will be injected subcutaneously (sc) in the right supra scapular area (Sharma et al., 1999, *J Immunol;* 163:5020-5028). Tumor growth will be monitored three times a week using a caliper. Once the tumor sizes reach to 8 mm in diameter (the larger diameter, not the smaller diameter), $10^6$ pfu viruses in up to 50 μl volume will be injected into the tumors directly. If needed, up to $10^{10}$ pfu may be used. The mice will be monitored daily initially. If the size of the tumor is not reduced in one week, additional injection of the viruses will be carried out. The experiment will be terminated when the tumor reaches 15 mm in diameter (the large diameter). Localization and titers of viruses will be examined as described above. In addition, samples of tumors and adjacent tissues will be collected for histopathology studies and for examination of presence of virus as well as tumor biology and immune responses as described in previous section. In additional experiments, a recombinant PIV5 with a combination of different mutations of PIV5 such as rPIV5ΔSH-CPI–, or rPIV5ΔSH-Rev may be generated and tested using the same experimental regiment.

Repeated injections of PIV5 into wild type mice do not cause any noticeable illness and mice seem to tolerate the injections well. Previous reports indicate that innate immune responses play a critical role in controlling PIV5 infection in mouse (He et al., 2002, *Virology;* 303:15-32; and He et al., 2001, *J Virol;* 75:4068-4079). Because nude mouse, like wild type mouse, has normal innate immune responses, it is expected that PIV5 will behave similarly in wild type mouse (immune competent mouse) to nude mouse in terms of tolerating PIV5 infection as well as allowing PIV5 replication in cancer cells but restricting PIV5 replication in normal cells.

Example 6

Oncolytic Activities of PIV5 Expressing MDA-7/IL-24

MDA-7, also known as IL-24, is a member of IL-10 cytokine family. It has been demonstrated that MDA-7/IL-24 can selectively induce apoptosis in many human cancer cell lines with minimum damage to normal cells and MDA-7/IL-24 can also inhibit growth of human cancer cell xenografts in a nude mouse model system (Nishikawa et al., 2004, *Oncogene;* 23 (42):7125-31; Yacoub et al., 2004, *Cancer Biol Ther;* 3(8):739-51; Nishikawa et al., 2004, *Mol Ther;* 9:818-828; Gopalkrishnan et al., 2004, *Int Immunopharmacol;* 4:635-647; and Ramesh et al., 2004, *Mol Ther;* 9:510-518 76-80). Results from phrase I/II clinical trials using MDA-7/IL-24 indicate MDA-7/IL-24 is safe and effective against solid tumor and melanomas (Introgen Therapeutics, Inc., Austin, Tex.).

The mechanism of selective killing of cancer cells by MDA-7/IL-24 is not clear. It is thought that multiple apoptotic pathways are activated by MDA-7/IL-24 (Wang et al., 2002, *J Biol Chem;* 277:7341-7347). At physiological levels, secreted MDA-7/IL-24 can interact with heterodimers of IL-20R1/R2 or IL-22R1/IL-20R2 and activate STAT-1 and STAT-3, leading to expression of genes that inhibit uncontrolled cell growth. When MDA-7/IL-24 is overexpressed, MDA-7/IL-24 can activate expression of GADD gene family and lead to apoptosis through intermediate proteins that are yet identified (Sauane et al., 2004, *Cancer Res;* 64:2988-2993).

While MDA-7 is known to preferentially kill tumor cells and clinical trials using IL-24 as an oncolytic agent have shown promise, the delivery of IL-24 to the desirable site at sufficient quantity remains a challenge. As described in Example 2, a recombinant PIV5 expressing MDA7 (rPIV5-MDA7) has been generated. To generate rPIV5-MDA7, a full-length MDA-7/IL-24 gene coding sequence (encoding 206 amino acid residues) that gives rise to secreted form of MDA-7/IL-24 was inserted into PIV5 genome between HN and L gene. This recombinant virus is very effective in killing tumors in vivo in a mouse model.

In this example, the oncolytic activity of rPIV5-MDA7 will be further tested. For example, the efficacies of a mutant PIV5 expressing the tumor killing agent MDA-7/IL-24 will be tested in treating metastatic breast cancer in a nude mouse model as well as in an immune competent mouse model system. In addition, the oncolytic activity of various mutant PIV5 constructs combined with MDA7 expression will be examined, to further enhance oncolytic activity of the viruses.

Negative strand RNA viruses, such as PIV5, initiate transcription from the 3' end leader sequence, and transcription levels of the viral genes are affected by their distances to the leader sequence. For example, the NP gene of PIV5 which is the closest to the leader sequence is the most abundantly transcribed, whereas the L gene that is the located most distance from the leader sequence is least transcribed. The efficacy of the oncolytic virus candidate may be enhanced by increasing the expression level of the MDA7 protein. To increase the expression level of the MDA7 gene, the MDA7 gene will be inserted immediately downstream of the leader sequence and upstream of the NP gene (PIV5-MDA7LN). The recombinant virus will be recovered and analyzed in vitro the same as PIV5-MDA7. Efficacy of PIV5-MDA7LN will be comparatively studied with that of PIV5-MDA7 in vitro and in vivo using solid tumor model and metastatic model in nude mice as well as immune competent model as described in the previous examples. Besides efficacy, the bio-distribution of the virus and tumor biology after virus infection will be examined. In addition, the expression of MDA7 in animals infected with rPIV5-MDA7 will be examined. In particular, the expression of MDA7 in tumors infected with rPIV5-MDA7 at 1, 3, 5 and 7 days post infection will be examined using immunoblotting. The expression of MDA7 in sera and internal organs such as lung, kidney and liver will also be examined.

Expression of MDA7 will be further combined with oncolytic activity of other mutants (for example, any of those described herein) to further improve efficacy of oncolytic activity of PIV5 as anti-tumor agents. For instance, a recombinant virus lacking the conserved C-terminus of V and expressing MDA7 (rPIV5 AC-MDA7) or containing even more mutations that are effective in enhancing oncolytic activity of PIV5 will be generated. The virus will be tested in solid tumor model, metastatic cancer model and LL2/C57/B16 model by examining efficacy, bio-distribution and tumor biology as described in the previous examples.

Example 7

The Role of AKT in Replication of PIV5

AKT (also known as protein kinase B, PKB) was first discovered in retrovirus AKT8 as a viral proto-oncogene capable of transforming certain cells (reviewed in Brazil and Hemmings, 2001, *Trends Biochem Sci;* 26:657-664). Identification and cloning of the AKT gene showed that it has high homology to protein kinases A and C, hence the name PKB. Three mammalian AKT genes (AKT1, 2 and 3, also known as PKBα, β, and γ, respectively) have been identified and they all have serine/threonine kinase activity. v-AKT is the viral form of AKT and is a fusion between the viral Gag and mouse AKT1. All AKT genes contain an N-terminal pleckstrin homology (PH) domain, a catalytic domain, and a C-terminal regulatory domain. There are two major phosphorylation sites within AKT, amino acid residue Thr308 and Ser473, which are phosphorylated by PDK1 (PI3K-dependent kinase 1) phosphorylates Thr308 and the rictor-mTOR complex respectively (Chan et al., 1999, *Annu Rev Biochem;* 68:965-1014; and Sarbassov et al., 2005, *Science;* 307:1098-1101). AKT has many downstream targets, including BAD, CREB, eNOS, I-KB kinase α, GSK-3 and p21 CIP1 (Du and Tsichlis, 2005, *Oncogene;* 24:7401-7409). AKT is a key regulator in the PI3K signaling pathway and plays an important role in many cellular processes such as cell survival, metabolism, growth, proliferation and mobility. AKT has been found to be activated in many cancers, and targeting AKT with small molecules has reduced tumor growth in some circumstances (Redaelli et al., 2006, *Mini Rev Med Chem;*

6:1127-1136; and Yoeli-Lerner and Toker, 2006, *Cell Cycle;* 5:603-605). It has been reported that AKT1 plays a critical role in breast cancer (Ju et al., 2007, *Proc Natl Acad Sci USA;* 104:7438-7443; and Sun et al., 2001, *Am J Pathol;* 159:431-437). While AKT1 and 2 are widely expressed in many organs and cell types, AKT3 is expressed preferentially, but not exclusively in neuronal cells. All three AKT genes share some redundant functions, but they all have distinct functions through the studies using knockout mice (single AKT knockout: Akt1−/− and Akt2−/− are viable, no report of Akt3 knockout yet) and siRNAs (Stambolic and Woodgett, 2006, *Trends Cell Biol;* 16:461-466).

Although it has been demonstrated experimentally that anti-tumor viruses can selectively kill tumor cells while causing minimum harm to normal cells, the mechanisms of this selectivity by anti-tumor viruses are not clear.

As shown in Example 2, an AKT inhibitor and siRNA inhibit PIV5 viral protein expression, the AKT inhibitor inhibits the reporter gene expression in the mini-genome system, and the AKT inhibitor has no effect on expression of viral proteins from mammalian gene expression vector using CMV promoter, indicating AKT likely plays a role in regulating viral RNA synthesis, not viral mRNA translation. Based on the results that AKT, a kinase that plays a critical role in cancer development, also plays a critical role in replication of PIV5, it is likely that AKT activation contributes to the selectivity of oncolytic virus. This example will test the role of AKT in PIV5 replication and the selectivity of PIV5. Elucidate the role of AKT in replication of PIV5. siRNA or small molecule inhibitor against AKT1 reduces replication of PIV5, indicating that AKT plays a critical role in replication of PIV5. However, the mechanism of regulation of PIV5 replication by AKT is not clear. AKT possibly plays a critical role in phosphorylation of the P protein of PIV5, which is an essential component of the viral RNA polymerase complex. The role of AKT in phosphorylation of P will be investigated and its consequences on virus replication. Understanding the role of AKT in virus replication will help with designing a more efficacious oncolytic virus. Preliminary studies indicate AKT, a kinase, plays a critical role in viral RNA synthesis. The role of AKT in virus replication will be tested. And the contribution of AKT to the selectivity of oncolytic virus (i.e., targeting cancer cells preferentially and causing minimal damage to normal cells, because of its dependence on AKT for efficient replication) will be tested. As demonstrated in the previous examples, siRNA or small molecule inhibitor against AKT1 reduces replication of PIV5, indicating that AKT plays a critical role in replication of PIV5. However, the mechanism of regulation of PIV5 replication by AKT is not clear. It is likely that AKT plays a critical role in phosphorylation of the P protein of PIV5, which is an essential component of the viral RNA polymerase complex.

This example will investigate the role of AKT in phosphorylation of P and its consequences on virus replication. Understanding the role of AKT in virus replication will help with designing a more efficacious oncolytic virus.

To determine whether AKT plays a role in regulating viral RNA synthesis, cells will be infected with PIV5 at 5 MOIs or mock-infected and at 1 dpi the cells will be treated with actinomycin D (Act D), which inhibits host RNA synthesis but has no effect on viral RNA synthesis, and AKT inhibitor or DMSO with $^{3}$H-UTP for 6 to 8 hours. The cells will be lysed with 1% SDS, mixed with the same volume of cold trichlotoacetic acid (TCA) (10%) and incubated on ice for 30 minutes. TCA-insoluble precipitates will be collected on glass filters (GF/C, 2.4-cm; Whatman), washed with 5% cold TCA and ethanol. The radioactivity on the filters will be measured using a scintillation counter as described in Kim et al (Kim and Kawai, 1998, *Biol Pharm Bull;* 21:498-505). Total RNA can also be extracted from the cells as described before using Qiagen RNA purification kit (Lin et al., 2005,

*Virology;* 338:270-280) and newly synthesized, 3H-labeled viral RNA will be measured using a scintillation counter. To further determine the effect of AKT inhibitor on RNA synthesis (transcription vs. replication), the cells labeled with 3H-UTP as described before will be lysed with a mild lysis buffer containing 0.5% Triton X-100 and 50 mM Tris-Cl (pH 7.4) (not to disrupt RNP, NP-encapsidated RNA structure). Half of the lysis will be treated with RNase A, which degrades viral mRNA as well as host RNA but not viral genome RNA since Npencapsidated RNA genome is resistant to RNase A treatment, the other half will be used as control. The radioactivity will be measured with a scintillation counter. Alternatively, viral genomic RNA will be obtained as described in Lin et al using immuno-precipitation with antibody against NP (Lin et al., 2005, *Virology;* 338:270-280) or from pellet fraction as described in Randall et al. (Randall and Bermingham, 1996, *Virology;* 224:121-129). In general, viral mRNA contains polyA tail and can be purified using polydT; whereas viral genome RNA that is encapsidated can be purified away from other RNA by anti-NP antibody or by centrifugation in ultra-centrifuge because of RNP (genome RNA and NP) can be pelleted due to its weight and density.

If AKT affects viral RNA replication, it may result in reduced viral mRNA expression due to the reduced amount of viral RNA genome template available for transcription. To measure the role of AKT on viral transcription directly, the minigenome system with a defective anti-genome promoter may be used. In this system, only viral RNA transcription will be measured since no viral RNA replication can occur due to the mutation in the anti-genomic promoter.

To determine whether AKT plays a role in termination/reinitiation during viral RNA synthesis, a mini-genome with two reporter genes has been constructed and will be tested. If the effect of AKT inhibitor is limited to initiation, the ratio of activities from two reporter genes will be similar between DMSO and AKT inhibitor treated cells, even though overall reporter gene activities of AKT inhibitor-treated cells would be lower than that of DMSO-treat cells. If AKT has a role in termination/reinitiation of viral mRNA transcription, the ratios of expression levels of two reporter genes will be very different between DMSO and AKT inhibitor treated cells. If AKT plays a role in elongation/processivity, ratios of R-Luc to F-Luc from the mini-genome system will be different between DMSO and AKT inhibitors because the second reporter gene in the mini-genome will be transcribed less due to lower processivity in the presence of AKT inhibitors.

Effects of AKT inhibitors on transcription termination and reinitiation can also be examined in PIV5-infected cells using quantitative real time PCR (qRT-PCR). If AKT plays a role in RNA replication, effects of AKT inhibitors on synthesis of vRNA (genomic RNA) or cRNA (anti-genomic sense RNA) can be detected with qRTPCR by measuring relative amount of vRNA and cRNA within NP-encapsidated genome RNA. Also, effects of AKT inhibitors on initiation of replication vs. elongation of replication can also be examined using qRT-PCR.

If a reduced amount of genome RNA is detected in the presence of AKT inhibitor, it may indicate that AKT plays a role in synthesis of viral genome RNA (replication). It is possible that inhibition of AKT may result in reduced viral RNA replication but increased viral mRNA synthesis. In this case, increased ratio of viral mRNA vs. viral RNA (vRNA or cRNA) may be observed. In case AKT affects initiation of viral RNA replication or transcription, more RNAs close to leader and trailer sequences may be detected.

Phosphorylation Status of AKT, NP, P and L. AKT inhibitors known to inhibit AKT phosphorylation such as the AKTIV inhibitor inhibited viral RNA synthesis (Kau et al., 2003, *Cancer Cell;* 4:463-476), indicating phosphorylation of AKT is important for its role in viral RNA synthesis. However, since some of the inhibitors can prevent phosphorylation of AKT by preventing conformation change associated with phosphorylation, it is possible that phosphorylation per se is not required for AKT's role in viral RNA synthesis. To determine the role of phosphorylation of AKT in viral RNA synthesis, phosphorylation status of AKT will be determined in mock and PIV5-infected cells. To determine whether phosphorylation of AKT is required for its role in viral RNA synthesis, siRNA targeting endogenous AKT 1 will be used. The cells will then be supplemented with a kinase inactive mutant AKT (Thr308Ala or Ser374Ala or both) or wild type AKT that contain changed nucleotide coding sequences without changing amino acid sequences to be resistant to the siRNA from an expression vector. If kinase inactive mutants can rescue the reduction of PIV5 replication caused by siRNA against endogenous AKT, it would indicate kinase activity of AKT is not required for its function in viral RNA synthesis. In addition, the effect of a dominant negative mutant of AKT 1 (AKT1DN) (van Weeren et al., 1998, *J Biol Chem;* 273:13150-13156) will be tested in PIV5-infected cells as well as in the mini-genome system.

In PIV5 infected cells, P is phosphorylated. In paramyxovirus Sendai virus, NP is phosphorylated as well (Lamb and Choppin, 1977, *Virology;* 81:382-397). Phosphorylation status of L is not clear. To determine the effect of AKT on their phosphorylation, phosphorylation status of NP, P and L in the absence as well as in the presence of AKT inhibitor will be examined. The cells will be infected with PIV5 at 5 MOIs or mock infected. At 1 dpi, the cells will be treated with DMSO or AKT inhibitor and labeled with $^{33}$P-phosphor or $^{35}$S-Met and $^{35}$S-cys for 6 to 8 hours. The cells will be then precipitated with antibodies against NP, P, L or AKT. Total amount of NP, P, L and AKT synthesized during the time period will be indicated by amount of $^{35}$S-labeled protein and amount of phosphorylated form of NP, P, L and AKT will be indicated by amount of $^{33}$P-labeled NP, P, L and AKT. It is possible that phosphorylation status of P changes over the course of infection. To examine the phosphorylation of NP, P, L and AKT over time, a time course of the experiment will be carried out. To directly measure the effect of AKT on phosphorylation of NP, P and L, a plasmid encoding NP, P or L will be transfected alone or with a plasmid encoding AKT 1. The cells will then be labeled with $^{33}$P-orthophosphor or $^{35}$S-Met and $^{35}$S-Cys as well as treated with AKT inhibitor or DMSO as before. Phosphorylated form and total amount of NP, P, L and AKT will be determined using immunoprecipitation with antibodies against NP, P, L or AKT.

Mapping the AKT phosphorylation site within P of PIV5 and determine the role of phosphorylation of P by AKT in viral RNA synthesis. In the previous examples it was shown that the P protein is phosphorylated in infected cells and AKT inhibitor can inhibit this phosphorylation. Importantly, AKT phosphorylates recombinant P purified from bacteria. However, exact phosphorylation sites of P of PIV5 are not clear. To study the impact of AKT mediated phosphorylation of the P protein by a more direct approach, phosphorylation sites of AKT within the P protein will be determined and then the effects of mutating these sites will be examined. P is highly enriched in threonine and serine residues (36 Ser and 32 Thr). To determine the sites, the P protein will be purified from infected cells. Purified P will be subjected to mass spectrometry (MS) analysis and phosphorylation sites will thus be determined. In case MS is not sufficient to pinpoint the sites for phosphorylation, mutations of suspected sites will be generated and tested. For instance, if a trypsin-digested peptide of P is identified as phosphorylated and the peptide happens to have more than one Ser or Thr residues, the Ser or Thr residues will be mutated to Ala individually, the mutant P proteins will be purified and subjected to the same MS analysis if a direct $^{33}$P-orthophosphor-labeling experiment is not sufficient to detect the differences of phosphorylation between wild type and mutant P proteins. In addition, a mutational analysis of the P protein will be carried out using bacteria purified protein with in vitro kinase assay by analyzing phosphorylation of P with deletion as well as point mutation to determine the phosphorylation site of AKT within P.

If the AKT phosphorylation sites of P are determined, mutations affecting phosphorylation of P will be generated and the effect of AKT inhibitor on phosphorylation status will be examined. If AKT affects the phosphorylation of P, AKT inhibitors would inhibit phosphorylation of the sites in vitro kinase assay. To determine the importance of these phosphorylation sites in viral RNA synthesis, the sites will be mutated and the effect of the mutations will be examined using the mini-genome system with functional leader and trailer sequences, which RNA transcription and replication can be tested as, and the mini-genome system with the defective anti-genome promoter, which only viral transcription can be examined as previously described (Lin et al., 2005, *Virology;* 338:270-280). Further, the effect of the mutations will be examined using reverse genetics system, if the mutations are not lethal. A similar approach will be followed to determine phosphorylation sites of V, NP and L and the roles of their phosphorylation in viral RNA synthesis if they are phosphorylated.

Ongoing experiments on determining phosphorylation sites of P have been productive; one phosphorylation site has been identified and another site has been mapped to a small peptide with two serine residues. Determining phosphorylation sites and their function is a challenging task. Such studies will focus first on the P protein. If phosphorylation of P is not important for its function, an unlikely possibility, focus will shift to the NP protein. Finally the L protein will be studied. Because of its size of L, it may be necessary to break the L protein down into different domains for analysis. The L protein may be expressed as two proteins: one containing domains 1, 2 and 3 (L123); and the other containing domains 4, 5 and 6 (L456). Whether L123 or L456 is phosphorylated and how AKT affects its phosphorylation will be determined as described above. L123 or L456 can be further reduced to small protein such as L12, which only contains domain 1 and 2. L is likely organized as 6 domains. Alternatively, to determine the phosphorylation sites using MS, purified virions can be used to obtain sufficient amount of viral proteins.

Examine the interactions between AKT and NP, P or L. It is possible that AKT affects phosphorylation of P or NP or L through an intermediate host factor in infected cells. It is also possible that AKT interacts with NP, P or L directly. To examine whether AKT interacts with viral RNA synthesis machinery, NP, P or L directly, coimmunoprecipitation (co-IP) will be carried out in infected cells as well as in cells transfected with AKT plus NP, P or L as previously described. In addition, the interactions will be detected in the presence of AKT inhibitors to investigate the effects of inhibitor on AKT and its interacting partners. To detect weak interaction, cross-linking reagents will be utilized. If interactions are detected between AKT1 and NP, P or L in transfected cells, whether AKT interacts directly with NP, P or L will be examined using purified proteins for determining direct interaction between V and AKT1.

Co-IP using infected cells provides knowledge in real infection and the result is preferred. However, because NP interacts with P and P interacts with L, it may not be possible to dissect interactions between AKT and any of the NP, P or L protein in infected cells without interference from each other. Co-IP of transfected cells thus provides a clear means to determine whether AKT can interact with NP, P or L without other viral protein. Whether addition of any component will further enhance the interaction will be examined if it is found one of them (NP, P or L) interacts with AKT. For instance, if AKT interacts with P, NP or L or both will be added to the transfection mixture to see whether there is enhancement of the interaction between P and AKT. In preliminary studies, AKT phosphorylates recombinant P protein purified from bacteria, indicating AKT can interact directly with P that is purified from bacteria. Thus, the detection of a P and AKT interaction in infected mammalian cells is expected.

The role of activated AKT in efficient virus replication and oncolytic activity of PIV5 without AKT phosphorylation site. AKT plays an essential role in efficient virus replication in cancer cells such as HeLa. In addition, the virus replicates better in cancer cells than normal cells in vivo. It is not clear whether an overactive AKT is sufficient to convert non-hospitable normal cells into susceptible cells. To test this, an active AKT will be expressed in normal cells and examine virus replication in the newly established cells in vivo. Towards this end, a lentiviral vector will be generated expressing a bicistronic mRNA containing a constitutively active AKT (T308E and S473D) and a GFP that are separated by an internal ribosome entry site (IRES) from EMCV (EIRES). The hTERT cells (normal HMEC immortalized with hTERT) will be transduced with the vector (a lentiviral vector with only EIRES and GFP will be used as a control) and the transduced cells will be sorted by the expression of GFP. The sorted cells will then be injected into nude mice.

In addition, MDA-MB-435 cells will be injected into nude mice as well (total three kinds of cells in equal numbers will be injected into each nude mouse at different locations). The cells will be infected with rPIV5-RL in situ and replication of rPIV5-RL will be monitored using an IVIS camera. If AKT phosphorylation site within P is determined as described above, a recombinant PIV5 containing a defective AKT phosphorylation site will be generated. The efficacy of this virus in reducing tumor growth will be examined in a similar fashion.

Consistent with published reports indicating that AKT is activated in MDA-MB-435 cells, the previous examples compared levels of phosphorylation of AKT in the hTERT and MDAMB-435 cell and found higher levels of AKT phosphorylation in MDA-MB-435 cells than that in the hTert cells. If activated AKT is sufficient for efficient virus replication, renilla luciferase activities from the hTERT cells with constitutively active AKT will be higher than the hTERT cells with only GFP in vivo. However, if renilla luciferase activities from the hTERT cells with constitutively active AKT are similar to that of the hTERT cells with control (GFP only), it indicates that active AKT alone is not sufficient for efficient virus replication. Since it is known that efficient virus replication requires many host factors, expressing only active AKT in normal cells such as the hTERT cells may not be sufficient to convert non-hospitable normal cells into susceptible cells. For instance, a robust interferon signaling system in normal cells such as hTERT cells may prevent efficient virus replication even in the presence of activated AKT. Since AKT plays a critical role in virus replication, recombinant PIV5 lacking AKT phosphorylation site is likely to be defective in virus replication. If this virus has oncolytic activity, it may be less selective since it may not prefer cancer cells which often have activated AKT. Because the virus is likely to be defective in virus replication, it is likely that it is not as effective as wild type in reducing tumor growth. The understanding of the role of AKT in virus replication gained from this example will assist in the design of more efficacious oncolytic viruses.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of inducing tumor cell syncytia formation in a subject with a tumor, the method comprising administering to the subject a composition comprising an isolated parainfluenza virus 5 (PIV5) mutant in an amount effective to induce tumor cell syncytia, wherein the PIV5 mutant comprises a mutation lacking the C-terminus of the V protein (rPIV5VΔC) and further comprises a heterologous nucleotide sequence encoding a tumor killing heterologous polypeptide and/or heterologous RNA.

2. The method of claim 1, wherein the subject is a companion animal.

3. The method of claim 2, wherein the companion animal is a dog.

4. The method of claim 1, wherein the tumor is a primary tumor and/or a metastatic tumor.

5. The method of claim 1, wherein the tumor is selected from the group consisting of melanoma, basal cell carcinoma, colorectal cancer, pancreatic cancer, breast cancer, prostate cancer, lung cancer (including small-cell lung carcinoma and non-small-cell lung carcinoma), leukemia, lymphoma, sarcoma, ovarian cancer, Kaposi's sarcoma, Hodgkin's lymphoma, Non-Hodgkin's lymphoma, multiple myeloma, neuroblastoma, rhabdomyosarcoma, primary thrombocytosis, primary macroglobulinemia, small-cell lung tumors, primary brain tumors, stomach cancer, head and neck cancers, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, kidney cancer, endometrial cancer, glioblastoma, and adrenal cortical cancer.

6. The method of claim 1, wherein administration of PIV5 is intratumoral, subcutaneous, intravenous, intranasal, intraperitoneal, intracranial, oral, or in situ.

7. The method of claim 1 further comprising administration of an additional therapeutic agent.

8. The method of claim 1, wherein the tumor killing heterologous polypeptide comprises melanoma differentiation-associated gene-7 protein (MDA-7).

9. The method of claim 1, wherein the tumor is a malignant solid tumor.

10. The method of claim 9, wherein the malignant solid tumor comprises a sarcoma or a carcinoma.

11. The method of claim 6, wherein administration of PIV5 is intratumoral.

12. The method of claim 1, wherein the heterologous nucleotide sequence encodes a tumor suppressor gene.

13. The method of claim 1, wherein the heterologous nucleotide sequence encodes a polypeptide selected from the group consisting of melanoma differentiation-associated gene-7 protein (MDA-7), p53, BRCA1, BRCA2, ATM, retinoblastoma tumor suppressor gene (RB), and TSG101.

14. The method of claim 1, wherein the heterologous nucleotide sequence is inserted downstream of the leader sequence and upstream of the nucleocapsid protein (NP) gene of the PIV5 genome.

15. The method of claim 1, wherein the heterologous nucleotide sequence is inserted between the hemagglutinin-neuroaminidase (HN) gene and the large RNA polymerase protein (L) gene of the PIV5 genome.

16. The method of claim 1, wherein the PIV5 mutant replicates in tumor cells.

17. The method of claim 1, wherein the PIV5 mutant infects other tumor cells.

* * * * *